United States Patent [19]
Lennox et al.

[11] Patent Number: 5,919,191
[45] Date of Patent: Jul. 6, 1999

[54] ELECTRO-SURGICAL TISSUE REMOVAL

[75] Inventors: Charles D. Lennox, Hudson, N.H.; Stephen F. Moreci, Milford; Troy W. Roberts, Pepperell, both of Mass.

[73] Assignee: Boston Scientific Corporation, Natick, Mass.

[21] Appl. No.: 08/794,209

[22] Filed: Jan. 30, 1997

Related U.S. Application Data

[63] Continuation-in-part of application No. 08/593,261, Jan. 29, 1996, abandoned, which is a continuation-in-part of application No. 08/379,908, Jan. 30, 1995, abandoned.

[51] Int. Cl.$^6$ .................................................... A61B 17/39
[52] U.S. Cl. ................................ 606/48; 606/46; 606/50
[58] Field of Search ................................ 606/48, 50, 46

[56] References Cited

U.S. PATENT DOCUMENTS

| | | | |
|---|---|---|---|
| 2,056,377 | 8/1936 | Wappler | 128/303.14 |
| 3,982,542 | 9/1976 | Ford et al. | 128/303.14 |
| 4,060,087 | 11/1977 | Hiltebrandt et al. | 128/303.15 |
| 4,116,198 | 9/1978 | Roos | 128/303.15 |
| 4,347,849 | 9/1982 | Congdon | 128/419 P |
| 4,538,610 | 9/1985 | Kubota | 128/303.15 |
| 4,648,399 | 3/1987 | Nakada | 128/303.14 |
| 4,674,499 | 6/1987 | Pao | 128/303.14 |
| 4,848,346 | 7/1989 | Crawford | 128/419 P |
| 4,917,082 | 4/1990 | Grossi et al. | 606/46 |
| 4,919,131 | 4/1990 | Grossi et al. | 606/46 |
| 4,934,367 | 6/1990 | Daglow et al. | 439/527 |
| 5,007,908 | 4/1991 | Rydell | 606/47 |
| 5,013,312 | 5/1991 | Parins et al. | 606/37 |
| 5,019,076 | 5/1991 | Yamanashi et al. | 606/45 |
| 5,029,573 | 7/1991 | Chow | 128/4 |

(List continued on next page.)

FOREIGN PATENT DOCUMENTS

| | | | |
|---|---|---|---|
| 0-544-392-A1 | 6/1993 | European Pat. Off. | A61B 17/39 |
| 3707820 | 9/1987 | Germany | A61B 17/36 |
| 2213381 | 8/1989 | United Kingdom | A61B 17/36 |
| WO93/13719 | 7/1993 | WIPO | A61B 17/39 |

OTHER PUBLICATIONS

American ACMI, "ACMI Adult Resectoscopes Operating & Maintenance Manual," Jun. 1984.
The Gray Sheet, vol. 22, Iss. 4, "Arthrocare Urological, Gynecological Electrosurgery Systems Under Review by FDA, Firm Says in IPO Filing; Launch of Core Arthrosopic System Begins," FDC Acc. No. 01220040006, Jan. 22, 1996.
Prior Teaching of Two Step Method.

*Primary Examiner*—Lee Cohen
*Attorney, Agent, or Firm*—Testa, Hurwitz & Thibeault, LLP

[57] ABSTRACT

The invention features a bipolar electro-surgical apparatus having a first electrode that has a relatively large surface area for creating a diffuse current sufficient to heat a region of tissue to coagulation temperatures and a second electrode that has a relatively small surface area for creating a concentrated current region sufficient to heat tissue adjacent to the second electrode to resection temperatures. The first and second electrodes are relatively positioned along a treatment path, such that tissue is coagulated and resected as the electro-surgical apparatus is disposed along the path. The invention also features a method for bipolar electro-surgical tissue removal including positioning a pair of bipolar electrodes along a treatment path, flushing the treatment path with an ionic fluid, and imposing a voltage differential to cause current to flow through tissue between the electrodes, where the current flowing through the tissue is sufficient to heat and cause coagulation of the tissue. The invention also features a method for bipolar electro-surgical tissue removal including attaching a power connector adaptor to a resectoscope that is configured for use with a monopolar electro-surgical device and inserting a bipolar electro-surgical device having bipolar electrodes into a working channel of the resectoscope, where the bipolar electro-surgical device is sized to fit within the working channel. The method further including electrically coupling the bipolar electrodes to the power connector adaptor.

4 Claims, 17 Drawing Sheets

U.S. PATENT DOCUMENTS

| | | | |
|---|---|---|---|
| 5,047,027 | 9/1991 | Rydell | 606/48 |
| 5,064,424 | 11/1991 | Bitrolf | 606/46 |
| 5,078,717 | 1/1992 | Parins et al. | 606/48 |
| 5,085,658 | 2/1992 | Meyer | 606/46 |
| 5,125,928 | 6/1992 | Parins et al. | 606/48 |
| 5,192,280 | 3/1993 | Parins | 606/48 |
| 5,196,011 | 3/1993 | Korth et al. | 606/46 |
| 5,197,964 | 3/1993 | Parins | 606/48 |
| 5,252,090 | 10/1993 | Giurtino et al. | 439/441 |
| 5,258,006 | 11/1993 | Rydell et al. | 606/205 |
| 5,269,780 | 12/1993 | Roos | 606/42 |
| 5,277,696 | 1/1994 | Hagen | 606/49 |
| 5,290,286 | 3/1994 | Parins | 606/50 |
| 5,403,311 | 4/1995 | Abele et al. | 606/49 |
| 5,484,435 | 1/1996 | Fleenor et al. | 606/46 |
| 5,514,130 | 5/1996 | Baker | 606/41 |

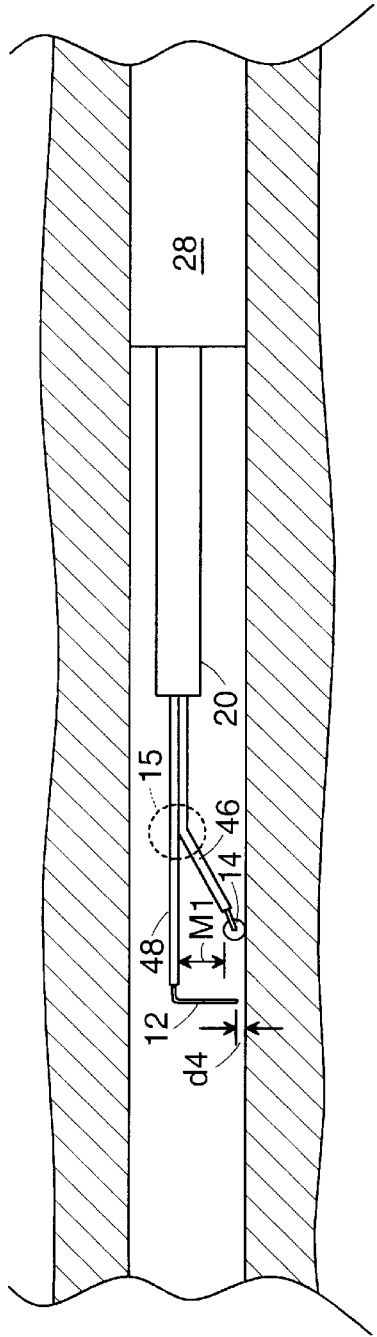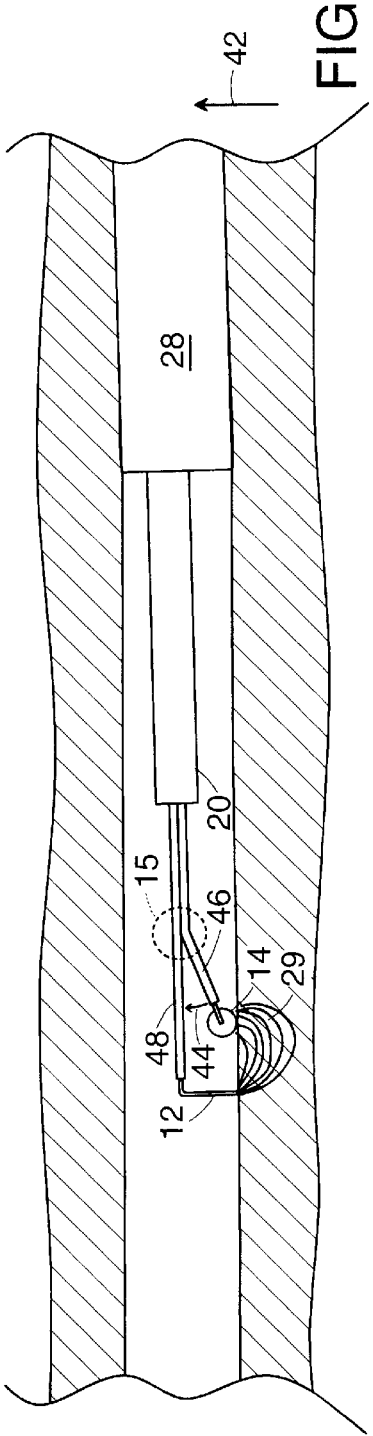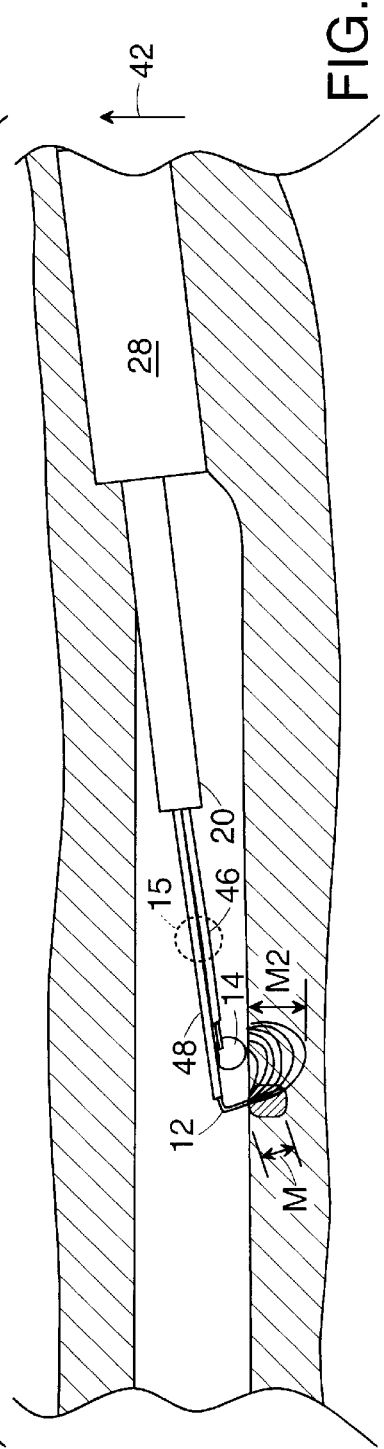

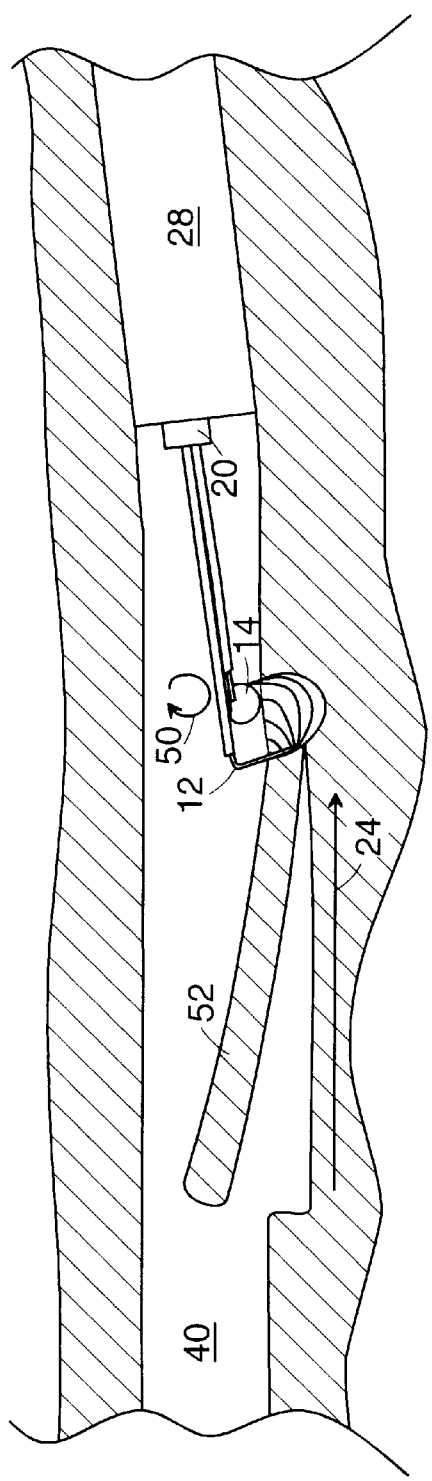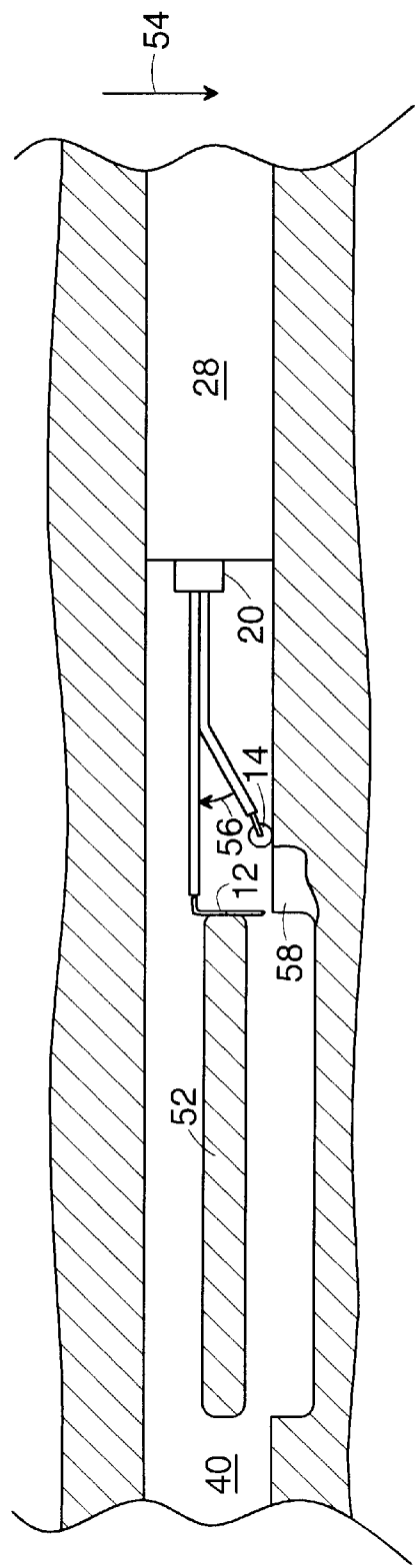

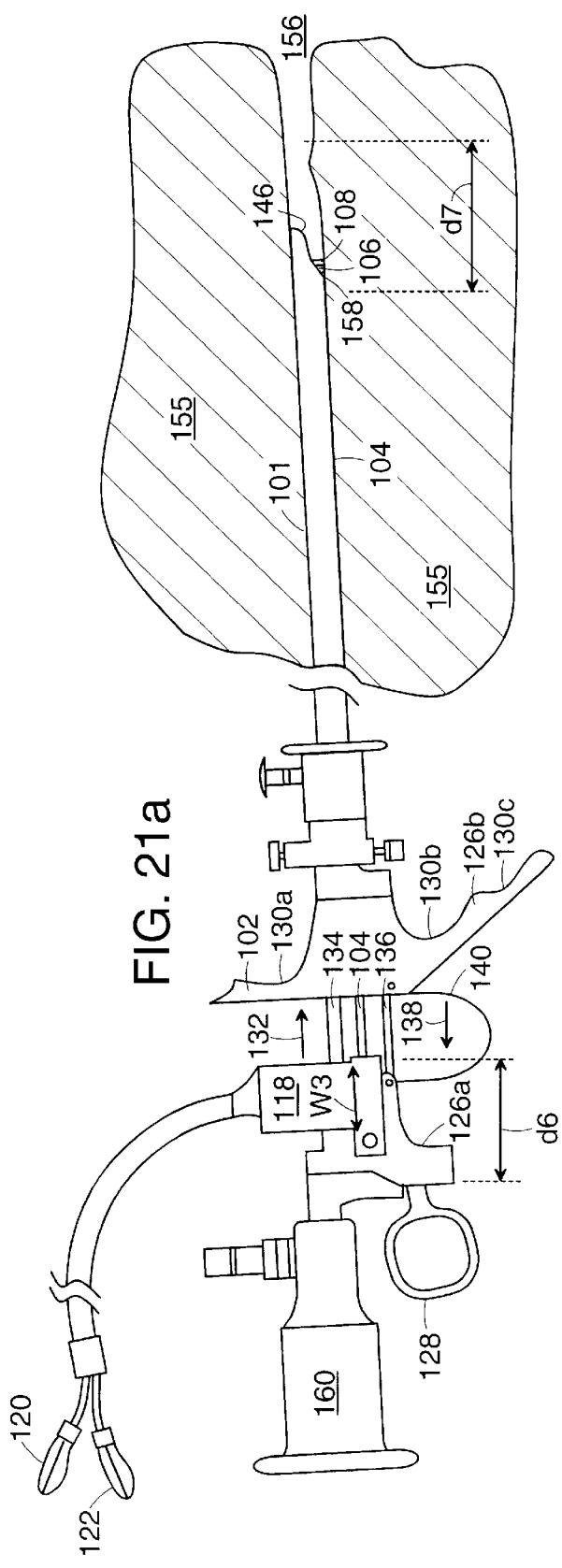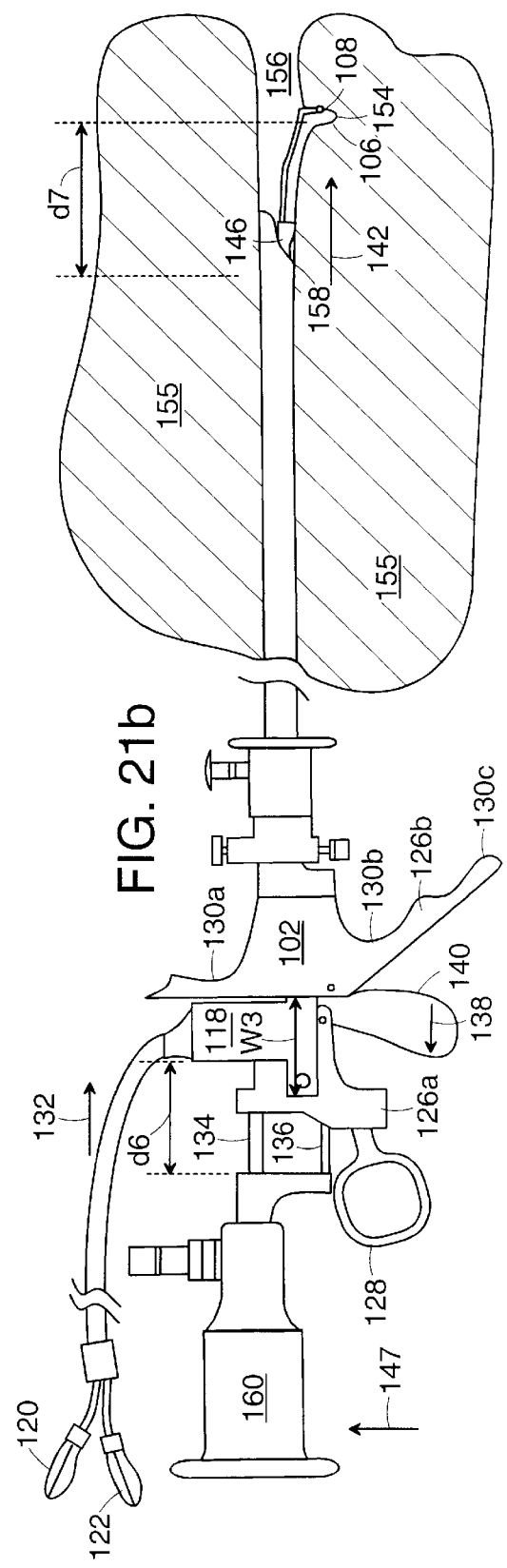

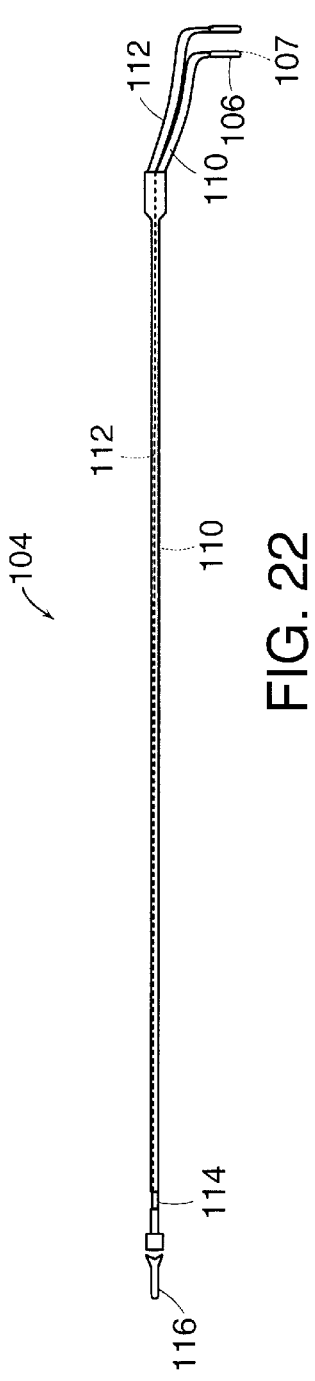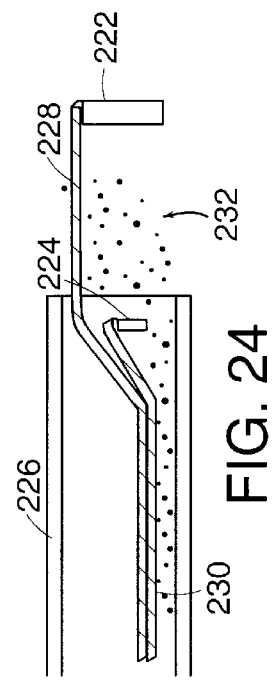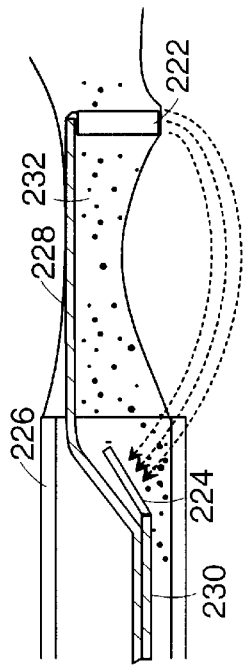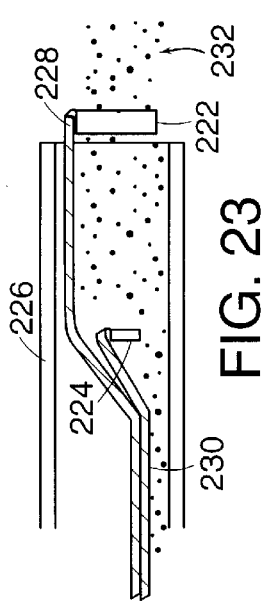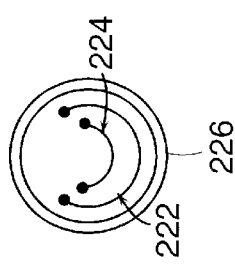

ELECTRO-SURGICAL TISSUE REMOVAL

CROSS REFERENCE TO RELATED APPLICATIONS

This application is a continuation-in-part of U.S. application Ser. No. 08/593,261, filed Jan. 29, 1996, abandoned which is a continuation-in-part of U.S. application Ser. No. 08/379,908, filed Jan. 30, 1995, abandoned.

FIELD OF THE INVENTION

This invention relates to electro-surgical tissue removal.

BACKGROUND

There are many medical procedures in which tissue is cut or carved away. For example, a transurethral resectioning of the prostate (TURP) is performed to treat benign or cancerous prostatic hyperplasia. Transurethral resectioning may also be performed in the bladder (TURB). The obstructing tissue can be resected with an electro-resectioning apparatus which is inserted into the urethra through a resectoscope. An electric current heats the tissue sufficiently to break intercellular bonds, cutting the tissue into strips or "chips" which are removed from the body through the resectoscope.

Extensive bleeding can occur as a result of electro-resectioning, which can obstruct the physician's view and lead to dangerous blood loss levels. Additionally, veins have a negative pressure and may take up ambient fluid when cut which can cause further complications. The bleeding can be treated or avoided by coagulating the tissue in the treatment area with an electrocoagulator that applies a low level current to denature cells to a sufficient depth without breaking intercellular bonds.

SUMMARY

In one aspect, the invention features a bipolar electro-surgical apparatus having a first electrode that has a relatively large surface area for creating a diffuse current zone sufficient to heat a region of tissue to coagulation temperatures and a second electrode that has a relatively small surface area for creating a concentrated current region sufficient to heat tissue adjacent to the second electrode to resection temperatures. The first and second electrodes are relatively positioned along a treatment path, such that tissue is coagulated and resected as the electro-surgical apparatus is disposed along the path.

Implementations of the invention may include the following features. The electrodes may be positioned such that coagulated tissue is resected as the apparatus is disposed along the treatment path, including positioning the first coagulating electrode proximally of the second resecting electrode. The electrodes may be coupled to permit pivoting to vary the depth of treatment, for instance, the electrodes may be coupled at a cantilever joint, and the mounting for the second electrode may be stiffer than the mounting for the first electrode. The apparatus may include a stop mechanism to limit the maximum depth of treatment. The electrodes may be substantially fixed to maintain their relative position along the treatment path, or they may be movable relative to each other along the treatment path. In addition, the electrodes may be movable to opposite sides of each other along the treatment path. The first electrode may be a roller electrode or a sled electrode, and the second electrode may be a loop electrode. The electro-surgical apparatus may be constructed for use with a resectoscope and may include a flow of fluid along at least one electrode surface for removing char.

In another aspect, the invention features a method for bipolar electro-surgical tissue removal. The method includes positioning a pair of bipolar electrodes along a treatment path and imposing a voltage differential to cause current to flow through tissue between the electrodes. The method also includes diffusing the current at a first electrode to heat the tissue sufficiently to cause coagulation and concentrating the current at a second electrode sufficiently to cause resection of the tissue. Further, the method includes moving the first and second electrodes along the treatment path, such that the tissue is coagulated and resected.

Implementations of the invention may include the following features. The second electrode may be moved in a direction substantially perpendicular to the tissue surface to vary the depth of treatment. The electrodes may be pivoted. The first electrode may be moved independent of the second electrode in an axial direction opposite to the direction of the treatment path and to an opposite side of the second electrode, and the electrodes may be moved along a new treatment path in the opposite direction, such that tissue is coagulated prior to being resecting. The maximum depth of tissue resected by the second electrode may be limited.

In another aspect, the invention features a bipolar electro-surgical apparatus including a roller electrode having a relatively large surface area for creating a diffuse current region sufficient to heat tissue to coagulation temperatures to coagulate a region of tissue and a loop electrode having a relatively small surface area for creating a concentrated current region sufficient to heat tissue adjacent the loop electrode and in the coagulation region to resection temperatures to resect the adjacent tissue. The roller electrode is positioned proximal to the loop electrode along a treatment path, such that tissue is coagulated prior to being resected to a desired depth as the device is moved along the treatment path, and the roller electrode is connected to the loop electrode.

In another aspect, the invention features a bipolar electro-surgical apparatus including a first electrode for coagulating tissue, and a second electrode coupled to the first electrode for simultaneously resecting tissue. When the resecting apparatus is moved along a treatment path, the second electrode resects tissue coagulated by the first electrode.

In another aspect, the invention features a resectoscope including a bipolar electro-surgical device having a first electrode with a relatively smaller surface area for creating a concentrated current region sufficient to heat tissue adjacent the first electrode to resection temperatures and a second electrode with a surface area which is larger than the surface area of the first electrode. The electrodes are positioned to coagulate and resect tissue adjacent to the electrodes as the electro-surgical device is moved along a treatment path.

In another aspect, the invention features a resectoscope including a bipolar electro-surgical device having a second electrode with a surface area which is slightly larger than the surface area of the first electrode, and the electrodes are positioned such that current passing between the electrodes creates a more diffuse current zone sufficient to heat a region of tissue to coagulation temperatures and such that tissue is coagulated and resected as the electro-surgical device is moved along a treatment path.

Implementations of the invention may include the following features. The resectoscope may include a power connector electrically coupled to the electrodes, where the resectoscope is constructed for used with a monopolar electro-surgical device.

In another aspect, the invention features a resectoscope including a working channel configured to receive an electro-surgical device having bipolar electrodes and a power connector configured to electrically couple two conductors to the bipolar electrodes.

Implementations of the invention may include the following features. The resectoscope may also include an electro-surgical device having bipolar electrodes, where a proximal portion of the electro-surgical device is configured for insertion within the working channel and the bipolar electrodes are configured for electrical connection to the power connector. The bipolar electrodes may include a first electrode having a relatively small surface area and a second electrode having a surface area which is slightly larger than the surface area of the first electrode. The bipolar electrodes may be loop electrodes.

In another aspect, the invention features an apparatus including a power connector adaptor configured for use with a bipolar electro-surgical device and configured for use with a resectoscope that is configured for use with a monopolar electro-surgical device.

Implementations of the invention may include the following features. The apparatus may also include a resectoscope configured for use with a monopolar electro-surgical device, and a bipolar electro-surgical device having bipolar electrodes, a proximal portion of the bipolar electro-surgical device configured to be inserted in a working channel of the resectoscope and the power connector adaptor configured to electrically couple a power source to the bipolar electrodes of the bipolar electro-surgical device. The bipolar electrodes may be loop electrodes.

In another aspect, the invention features a method for bipolar electro-surgical tissue removal including positioning a pair of bipolar electrodes along a treatment path in an ionic liquid environment and imposing a voltage differential to cause current to flow through tissue between the electrodes, where the current flowing through the tissue is sufficient to heat and cause coagulation of the tissue. The method further includes concentrating current at one of the bipolar electrodes, where the concentrated current is sufficient to resect tissue adjacent to the one of the bipolar electrodes, and moving the electrodes along the treatment path to coagulate and resect tissue.

Implementations of the invention may include the following features. The ionic liquid environment may be saline.

In another aspect, the invention features similar methods for resecting tissue from a patient's prostate, e.g., transurethral resectioning procedure of the prostate, and for resecting tissue from a patient's bladder, e.g., transurethral resectioning of a patient's bladder. Other similar methods include resecting tumors from walls of a patient's uterus, e.g., myomectomy, and resecting a portion of lining of a patient's uterus, e.g., endometrioma.

In another aspect, the invention features a method for bipolar electro-surgical tissue removal including attaching a power connector adaptor to a resectoscope that is configured for use with a monopolar electro-surgical device and inserting a bipolar electro-surgical device having bipolar electrodes into a working channel of the resectoscope, where the bipolar electro-surgical device is sized to fit within the working channel. The method further including electrically coupling the bipolar electrodes to the power connector adaptor.

Implementations of the invention may include the following features. The method may include electrically connecting the power connector adaptor to a power source. The method may also include positioning the bipolar electrodes along a treatment path, imposing a voltage differential to cause current to flow through tissue between the electrodes, where the current flowing through the tissue is sufficient to heat and cause coagulation of the tissue, concentrating current at one of the bipolar electrodes, where the concentrated current is sufficient to resect tissue adjacent to the one of the bipolar electrodes, and moving the electrodes along the treatment path, such that tissue is coagulated and resected. Before imposing a voltage differential, the method may include flushing the treatment path with an ionic fluid.

Embodiments of the invention may exhibit one or more of the following advantages. Tissue can be coagulated just prior to resection in a single step operation to effect substantially bloodless tissue removal which can reduce complications from blood loss, fluid absorption, time in surgery, and patient trauma. The operation can be carried out using a bipolar electro-surgical instrument that carries two, separate-function electrodes. One electrode concentrates current to cut tissue while the other diffuses the current to coagulate tissue. The electrodes are arranged along a line of treatment such that tissue can be automatically, coagulated immediately before resection. The electrodes may also be positioned relative to each other in directions transverse to the direction of treatment so that the depth of cut and coagulation can be controlled or preset, e.g., to prevent resection beyond the coagulation zone. Relatively high power, e.g., well above 60 watts, such as 100 watts or more, can be applied to effect deep tissue coagulation with low risk of injury to the patient because current is focused along a short path between the bipolar electrodes. The instrument can be constructed for use with a variety of existing surgical devices and can be easily manufactured.

Tissue may be resected and coagulated substantially simultaneously in an ionic, non-osmotic liquid environment, e.g., saline, to prevent complications, e.g., electrolyte imbalance, caused by excessive fluid absorption. The operation can be carried out using a bipolar electro-surgical instrument that carries two substantially similar electrodes. Applying a relatively high power, e.g., 150–300 Watts, to the electrodes causes current to pass and possibly an arc to form between the electrodes. One electrode is slightly smaller than the other electrode and concentrates current to cut tissue while the current passing between the two electrodes coagulates tissue adjacent to the incision. The bipolar electro-surgical instrument may be sized to fit within an existing resectoscope that is designed for use with a monopolar electro-surgical instrument, and together with a power connector adaptor that electrically couples the bipolar electrodes to a power source, an existing monopolar resectoscope is modified into a bipolar resectoscope.

Additional advantages and features are apparent from the following.

DETAILED DESCRIPTION

FIG. 1a is a perspective view of an electro-surgical device positioned within a resectoscope.

FIG. 1b is a perspective view of the electro-surgical device of FIG. 1a.

FIGS. 5–9 are cross-sectional side views of the distal portion of the electro-surgical device of FIG. 1a in use within a urethra.

FIGS. 21a–21c are cross-sectional side views of the electro-surgical device of FIG. 12 in use within a urethra.

FIG. 22 is a side view of another electro-surgical device that can be used in conjunction with the resectoscope of FIG. 12.

FIG. 23 is a side view of another electro-surgical device in a retracted position within a distal portion of a resectoscope.

FIG. 24 is a side view of the electro-surgical device of FIG. 23 in an extended position within the distal portion of the resectoscope.

FIG. 25 is a cross-sectional view of the electro-surgical device of FIG. 23 within the distal portion of the resectoscope.

FIG. 26 is a side view of another electro-surgical device in an extended position within the distal end of a resectoscope.

STRUCTURE

Figure 1:
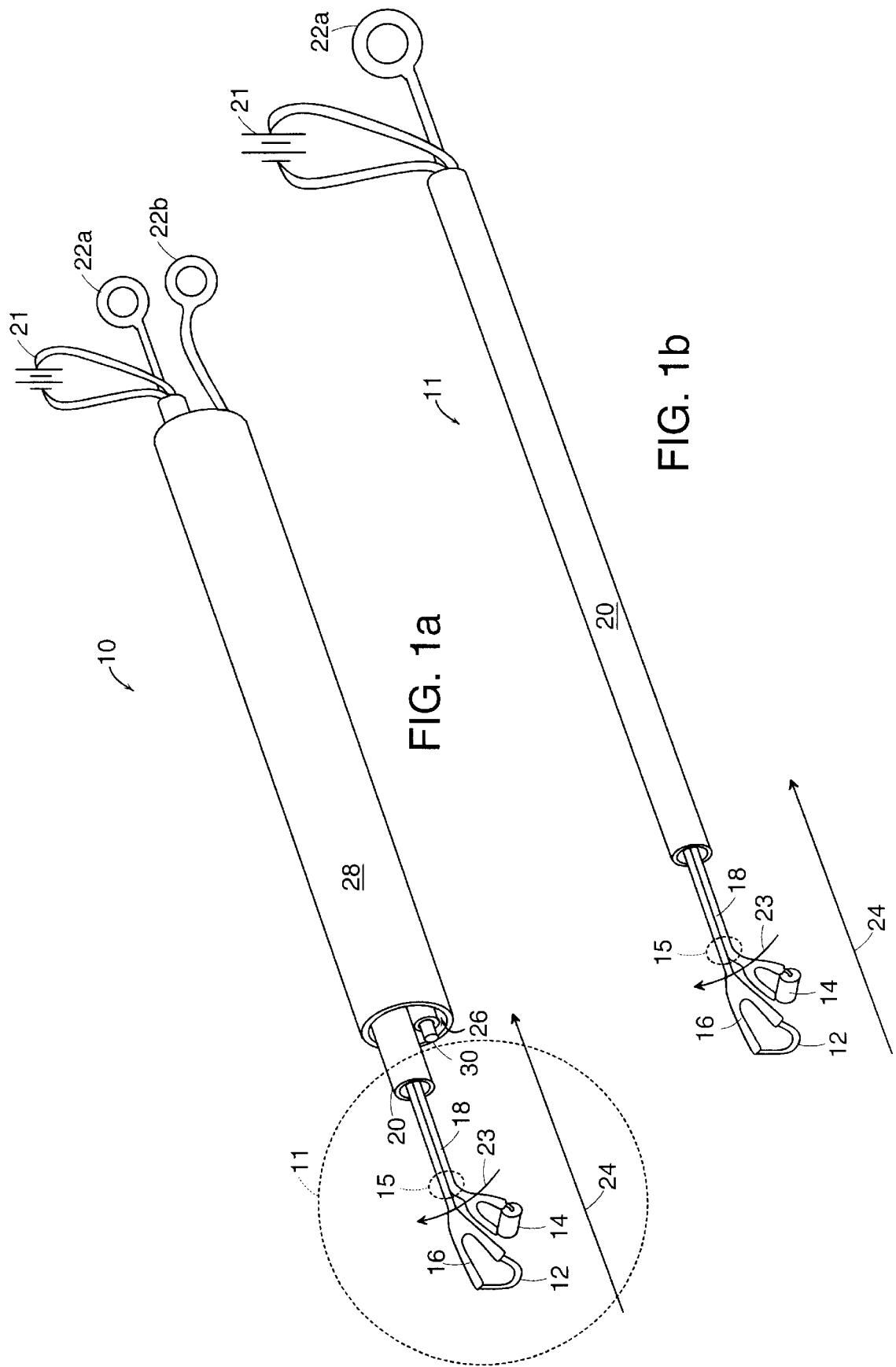

Referring to FIGS. 1–4, particularly to FIGS. 1a and 1b, a transurethral resection assembly 10 includes a resectoscope 28 and a bipolar electro-surgical device 11 having a loop-form resecting electrode 12 and a coagulating electrode 14. When power is applied to the device, the larger surface area of coagulating electrode 14 diffuses current to coagulate tissue over a large region while the smaller surface area of resecting electrode 12 concentrates current to resect immediately adjacent tissue. Since the coagulating electrode 14 is positioned ahead of the cutting electrode 12 along a line of resection 24, tissue is coagulated just prior to resection. Coagulating electrode 14 pivots (arrow 23) with respect to resecting electrode 12 through cantilever joint region 15 which controls the depth of resection and coagulation.

Figure 2:
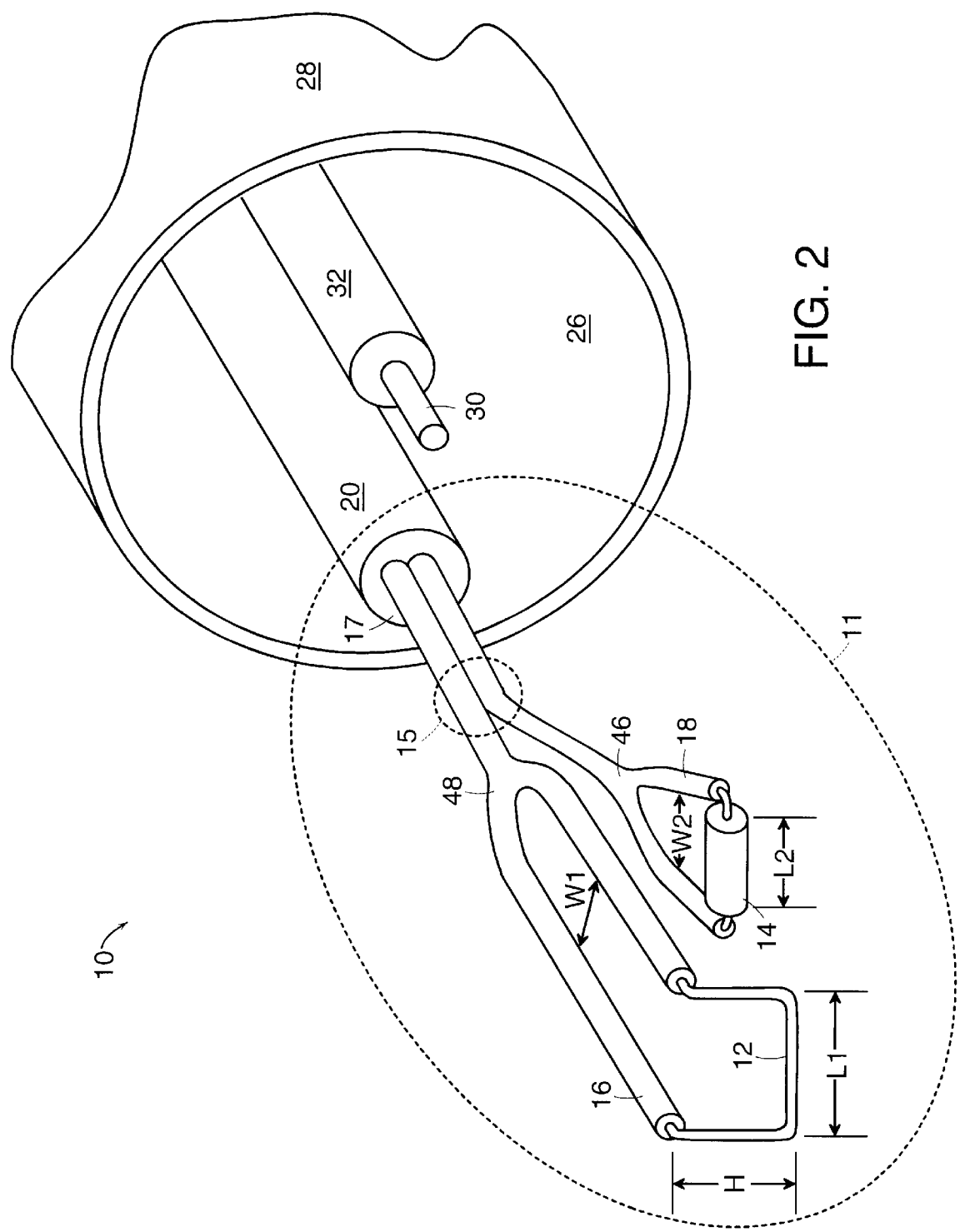
FIG. 2 is an enlarged perspective view of a distal portion of the electro-surgical device of FIG. 1.
Figure 3:
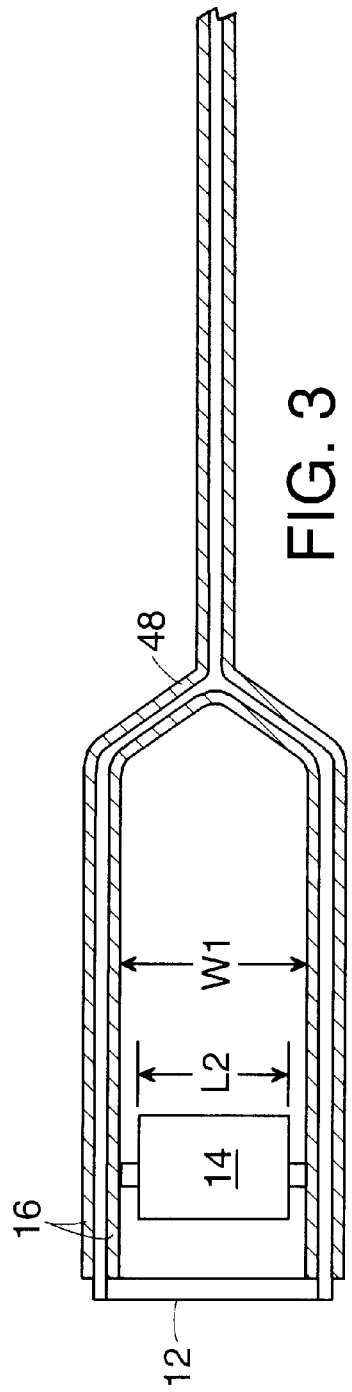
FIG. 3 is an enlarged top view of the distal portion of the electro-surgical device of FIG. 1.

Referring particularly to FIGS. 2 and 3, the width W2 of mounting fork 46 of coagulating electrode 14 and the width W1 of mounting fork 48 of resecting electrode 12 are substantially similar. As a result, mounting fork 48 engages mounting fork 46 to limit the maximum depth of resection to avoid resection of tissue beyond the coagulation zone, as will be described in more detail below.

Resecting electrode 12 and coagulating electrode 14 are connected by wire leads that extend through electrical insulator jackets 16, 18, to a power source 21 (RF generator). The insulated leads extend in close proximity through metal jacket 20 and are axially fixed relative to each other and jacket 20 by epoxy fill 17. Metal jacket 20 terminates proximally in articulation ring 22a. Ring 22b is connected (not shown) to resectoscope 28. Rings 22a and 22b are electrically insulated from the electrodes and enable a physician to move metal jacket 20 and, hence, the electrodes within lumenal space 26 of resectoscope 28 in an axial direction along the resecting path 24.

The resectoscope also includes a telescope 30 that images and illuminates resecting path 24. Telescope 30 is attached to metal jacket 20 through clip 32. As an alternative, separate lumens (i.e., one for metal jacket 20 and one for telescope 30) are provided within resectoscope 28. Additionally, lumenal space 26 is used to irrigate and displace fluid (i.e., urine in the urethra) in the area of resection. Preferably, lumenal space 26 is filled with a non-osmotic, non-electrolytic, high impedance fluid such as glycine (not shown). The non-osmotic nature of glycine reduces damaging cellular fluid absorption, and the non-electrolytic and high impedance nature of glycine insures that the current passed between the electrodes is focused in the tissue between the two electrodes.

To reduce the cost of the procedure, distilled water (i.e., deionized water) can be used instead of glycine. Like glycine, distilled water is non-electrolytic. However, unlike glycine, distilled water is osmotic. The substantially bloodless nature of the procedure, however, significantly reduces the amount of fluid absorbed by the patient. Hence, the osmotic nature of distilled water does not typically pose a danger.

Figure 4:
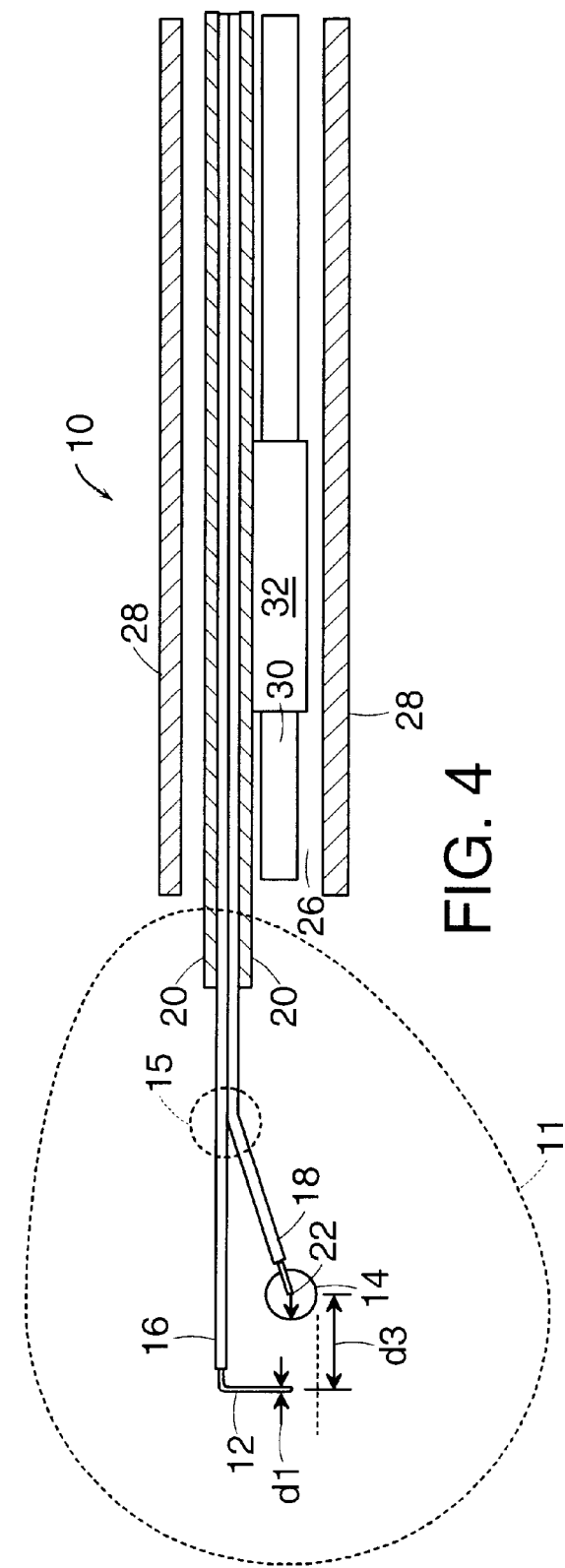
FIG. 4 is an enlarged cross-sectional side view of the distal portion of the electro-surgical device of FIG. 1.

In a particular embodiment, resecting electrode 12 is tungsten and coagulating electrode 14 is a silver/copper alloy, and the lead wires (not shown) within insulating jackets 16, 18, respectively, may be made of many materials, including brass, a copper alloy, or a silver alloy. Resecting electrode 12 has a loop-wire diameter dl of 0.012 inches (FIG. 4), a length L1 of 0.30 inches (FIG. 2), and a height H of 0.325 inches (FIG. 2). Coagulating electrode 14 is a cylindrical roller with a diameter d2 of about 0.125–0.187 inches (FIG. 4) and a length L2 of between 0.187–0.25 inches (FIG. 2). Electrodes 12 and 14 are separated by a distance d3 of approximately 0.187 inches (FIG. 4). Pivoting action of the electrodes can be facilitated by making the mounting fork 48 of resecting electrode 12 stiffer than the mounting fork of coagulating electrode 14, e.g., by using a stiffer wire within insulating jacket 18. Metal jacket 20 is made of stainless steel and has an outer diameter of about 0.068 inches, a wall thickness of about 0.005 inches, and an axial length of about 8.0 inches. The power source is a surgical radio frequency (RF) generator, generating a continuous sine wave (i.e., cut waveform) and operating at a typical frequency of 1MHz and at typical power levels of 100–300 Watts.

Use

Referring to FIGS. 5–9, the operation of electro-surgical device 11 will be described with regard to a transurethral resectioning procedure (TURP). The patient is prepared by inserting a resectoscope to the region of treatment. The physician, with a telescope and irrigation, inspects the region. The region is then flushed with glycine or distilled water.

Referring particularly to FIG. 5, the device 11 is inserted into the patient's urethra 40 through the resectoscope such that resecting electrode 12 and coagulating electrode 14 extend from resectoscope 28. When first inserted, cantilever joint 15 is fully open such that coagulating electrode 14 rests on the surface of tissue to be resected and resecting electrode 12 is suspended a slight distance d4, approximately 0.040 inches, above the surface of the tissue to be resected. The separation is a safety factor since, if power is accidentally applied, current will not pass between the electrodes in a glycine or distilled water environment until both electrodes contact the tissue surface.

Referring to FIG. 6, by applying an upward pressure to the external end of resectoscope 28, as indicated by arrow 42, the physician pivots coagulating electrode 14 with respect to resecting electrode 12, as indicated by arrow 44. This pivoting brings resecting electrode 12 into contact with the tissue to be cut and brings the fork 46 (FIG. 2) of coagulating electrode 14 closer to the fork 48 of resecting electrode 12.

Once both electrodes are in contact with the surface of the tissue to be cut, the physician applies power to the electrodes through hand or foot controls (not shown). As discussed, both electrodes 12 and 14 must contact the tissue because the surrounding glycine or distilled water will not conduct current. Current 50 flows through the tissue between the two electrodes. The projected surface area (i.e., shadow or tissue contact area) of coagulating electrode 14 is about 2–5 times larger than the projected surface area of resecting electrode 12. As a result, the current density at resecting electrode 12 is larger than the current density at coagulating electrode 14. The larger surface area of coagulating electrode 14 disburses current over a wide, deep area 29 and causes heating in the area sufficient only to coagulate the tissue (i.e., approximately 60–100° C.). On the other hand, the small surface area of resecting electrode 12 concentrates the current density and causes heating in adjacent tissue sufficient to resect the tissue. Typically, the heating induces a vigorous vaporization in the area immediately adjacent the electrode surface. (In some cases, a plasma arc may be generated in the area immediately adjacent the electrode with temperatures of approximately 1000° C. and above. However, lower temperatures, without arcing, can be used for resection.)

Referring to FIG. 7, when the physician increases the upward movement 42 of resectoscope 28, the electrodes pivot bringing electrically insulated forks 46, 48 in contact and causing resecting electrode 12 to resect the tissue to its maximum depth M1 (FIGS. 5 and 7). Since, the length L2 (FIG. 3) of coagulating electrode 14 is less than the width W1 of fork 48 the contact of both insulated forks limits the maximum depth of resection. The maximum depth of resection is limited to prevent resection beyond the depth of coagulation. When forks 46, 48 are in contact, approximately half of coagulating electrode 14 extends between the tines of fork 48. The large surface area and low current density of coagulating electrode 14 keeps coagulating electrode 14 from plunging into the tissue.

Approximately 100–300 Watts of power applied to the electrodes causes resecting electrode 12 to resect to a maximum depth M1 of about 0.20 inches (0.5 cm) and coagulating electrode 14 to coagulate to a maximum depth M2 of about 0.4 inches (1 cm). Coagulating 0.20 inches deeper than resection insures substantially bloodless resection.

Referring to FIG. 8, the physician squeezes articulation rings 22a and 22b together to pull the device 11 proximally. Coagulating electrode 14 rolls, as indicated by arrow 50, along resecting path 24 and resecting electrode 12 carves a chip 52 of tissue from urethra 40.

Referring to FIG. 9, in a typical transurethral procedure, the resecting path is from the bladder to the verumontanum in the prostate (approximately 1.5–10 inches). When the physician has reached the end of resection path 24 (i.e., the point where the physician wishes to stop resecting), either stops applying upward pressure to resectoscope 28 allowing urethra 40 to cause resectoscope 28 to move in a downward direction, indicated by arrow 54, or directly applies a downward force to move the resectoscope in the downward direction. This causes cantilever joint 15 to spring open, indicated by arrow 56, pivoting resecting electrode 12 upward and away from coagulating electrode 14. Because coagulating electrode 14 travels ahead of resecting electrode 12 along the resecting path 24, a small portion of coagulated tissue 58 remains in place (i.e., not resected). During the procedure, the resected chips are normally kept in the patient's bladder, and once the resection is completed, the patient's bladder is evacuated making sure to remove all of the resected chips.

Another Structure

Figure 12:
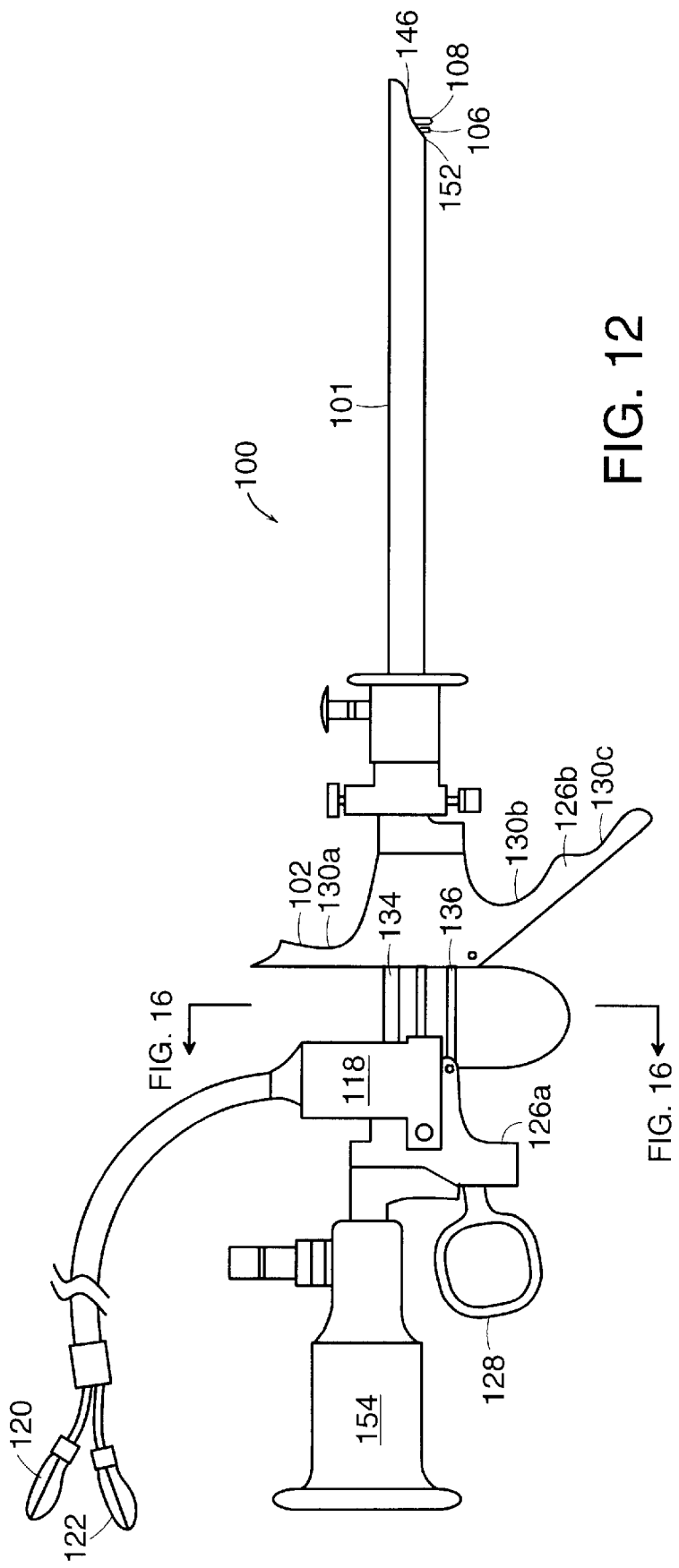
FIG. 12 is a side view of another resectoscope.
Figure 13:
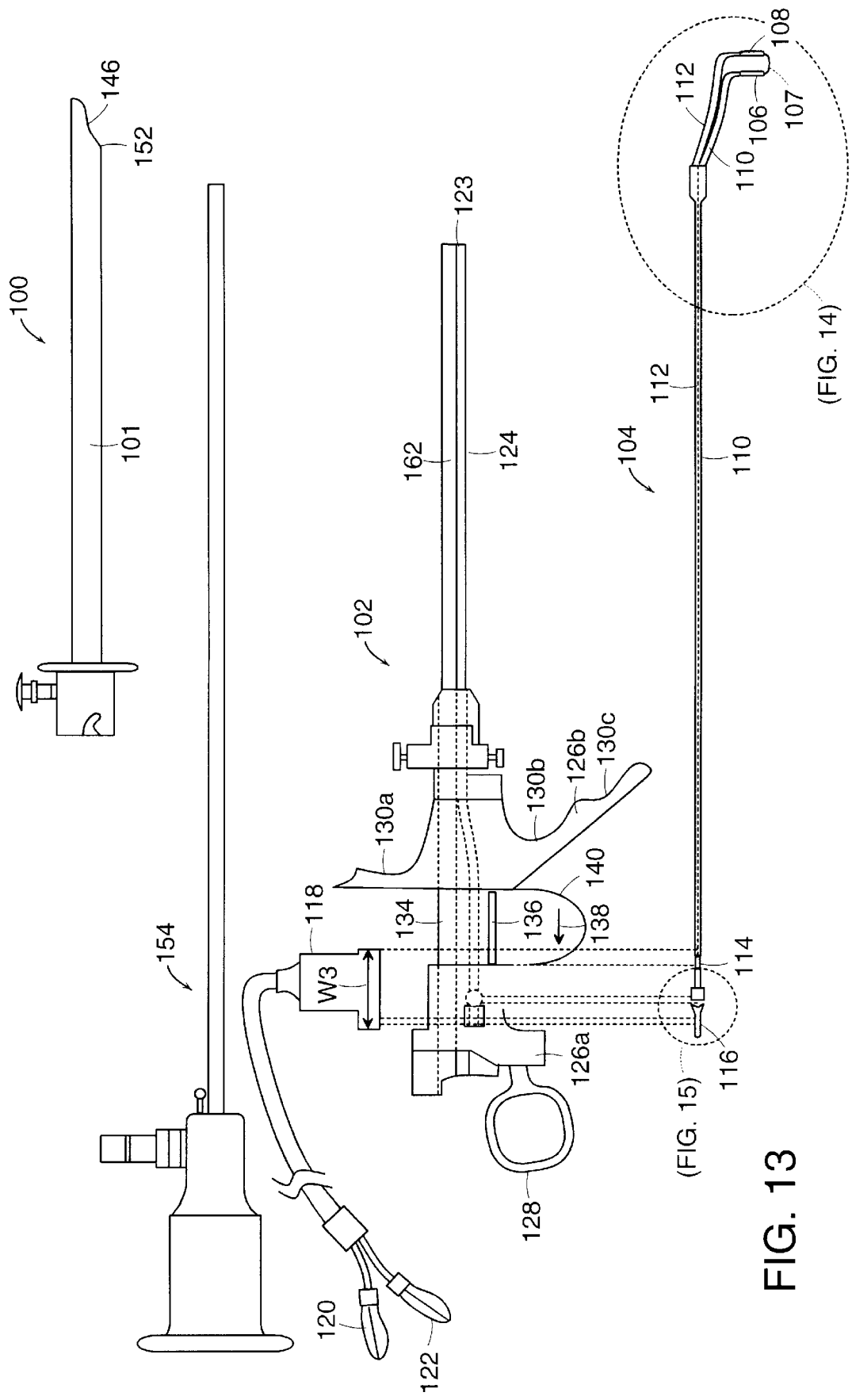
FIG. 13 is an exploded, side view of the resectoscope of FIG. 12.
Figure 14:
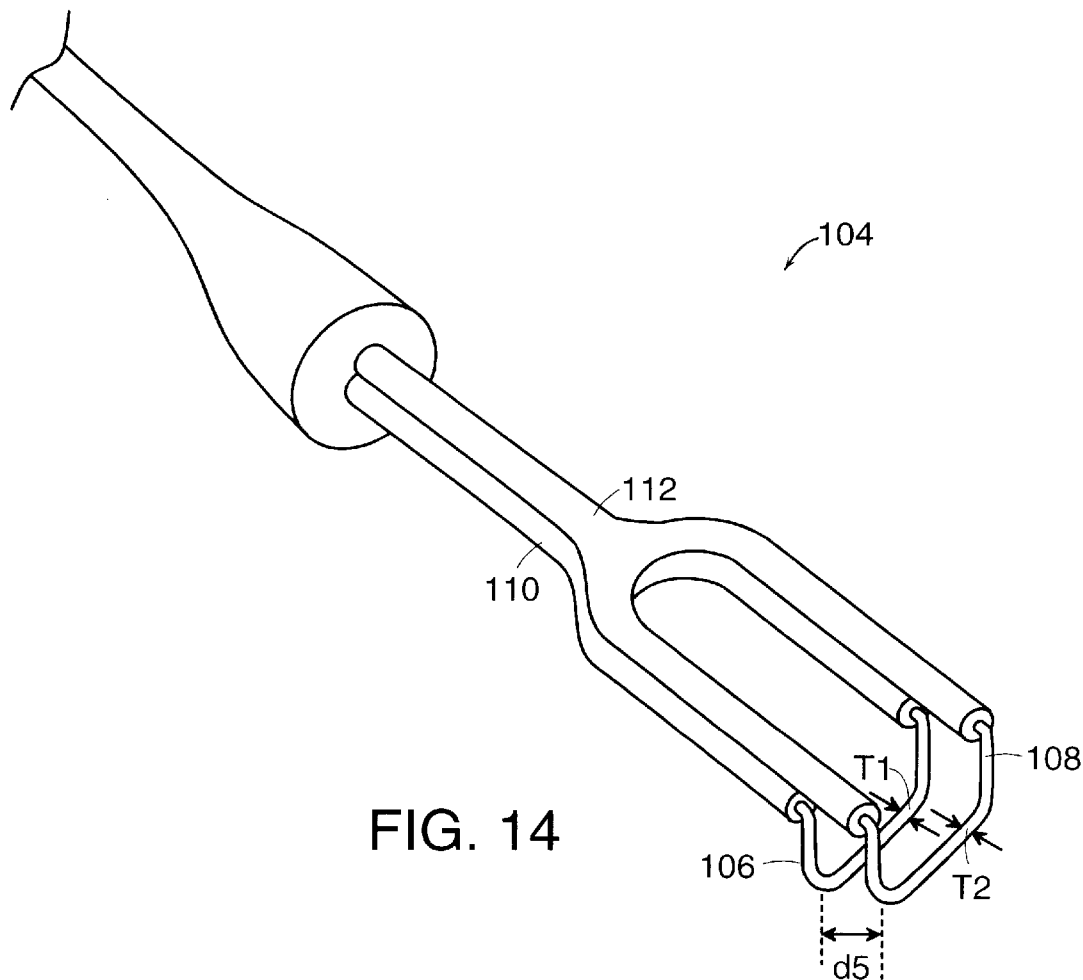
FIG. 14 is an enlarged perspective view of a distal portion of an electro-surgical device used in conjunction with the resectoscope of FIG. 12.

Referring to FIGS. 12–14, another transurethral resection assembly 100 includes an ACMI resectoscope 102 and a bipolar electro-surgical device 104 having two closely spaced, substantially similar loop-form electrodes 106, 108. The thickness T1, approximately 0.027", of loop electrode 106 is slightly smaller than the thickness T2, approximately 0.030", of loop electrode 108. As a result, loop electrode 106 is the hot or cutting electrode while loop electrode 108 is the cold or return electrode. Loop electrode 106 can be a wedge-shaped electrode of the type described in Hahnen, U.S. Pat. No. 5,569,244, the entire disclosure of which is hereby incorporated herein by reference. When power is applied to the device, loop electrode 106 concentrates the current density and causes heating in adjacent tissue sufficient to resect the tissue. The current 107 passing between the electrodes is dispersed over a region of tissue in the area of the incision and causes heating in the region sufficient only to coagulate the tissue in the region. By applying excessive power, approximately 125–300 Watts, to the electrodes, the tissue in the area of the incision may be coagulated to a depth sufficient to minimize or eliminate bleeding.

Spacing two substantially similar loop electrodes a small distance d5, e.g., 0.027", apart provides a low impedance path between the loop electrodes and insures that the current passing between the loop electrodes is confined to a short path. Confining the current path permits safe high power, e.g., 125–300 Watts, electro-surgery. Additionally, the electrodes are capable of resecting tissue in a conductive liquid environment, e.g., saline, because the current is focused in the tissue between the electrodes and is not disbursed through the conductive liquid.

Although coagulating tissue before or substantially simultaneously with tissue resectioning reduces fluid absorption via venous sinus, fluid absorption may still occur. For example, in a myomectomy procedure a tumor is resected from the uterus wall. Prior to tissue resectioning, the uterus is pressure distended with fluid which significantly increases the likelihood of excessive fluid absorption. Excessive absorption of non-ionic fluids such as glycine can lead to life-threatening electrolyte imbalance. Resecting tissue in an ionic liquid environment such as saline reduces the risk of electrolyte imbalance.

Figure 15:
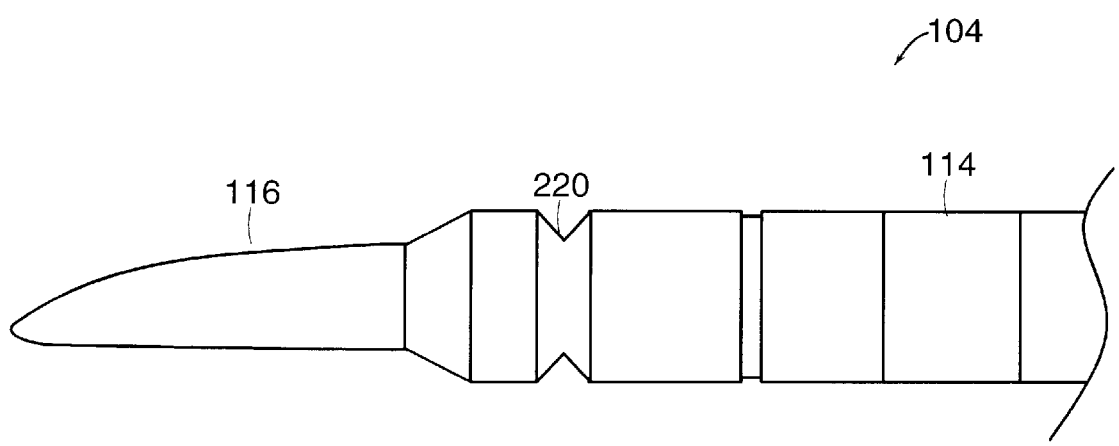
FIG. 15 is an enlarged side view of a proximal portion of the electro-surgical device used in conjunction with the resectoscope of FIG. 12.

With reference to FIGS. 13 and 15, loop electrodes 106, 108 are connected by wire leads that extend through electrical insulator jackets 110, 112 to platinum electrical contact ring 114 and brass or bronze electrical contact pin 116, respectively, which are mounted on the nylon shaft of bipolar electrosurgical device 104. Pin 116 includes a slot 220 that can be grasped by a knife edge lock in handle portion 126a, as described below. The insulated leads are axially fixed in parallel relative to each other. Bipolar electrosurgical device 104 is inserted into resectoscope 102 through a distal end 123 of a metal jacket 124 in resectoscope 102. A power connector 118 electrically couples ring 114 and pin 116 with banana plugs 120, 122, respectively. During operation, the banana plugs are connected to an RF generator (not shown).

Figure 16:
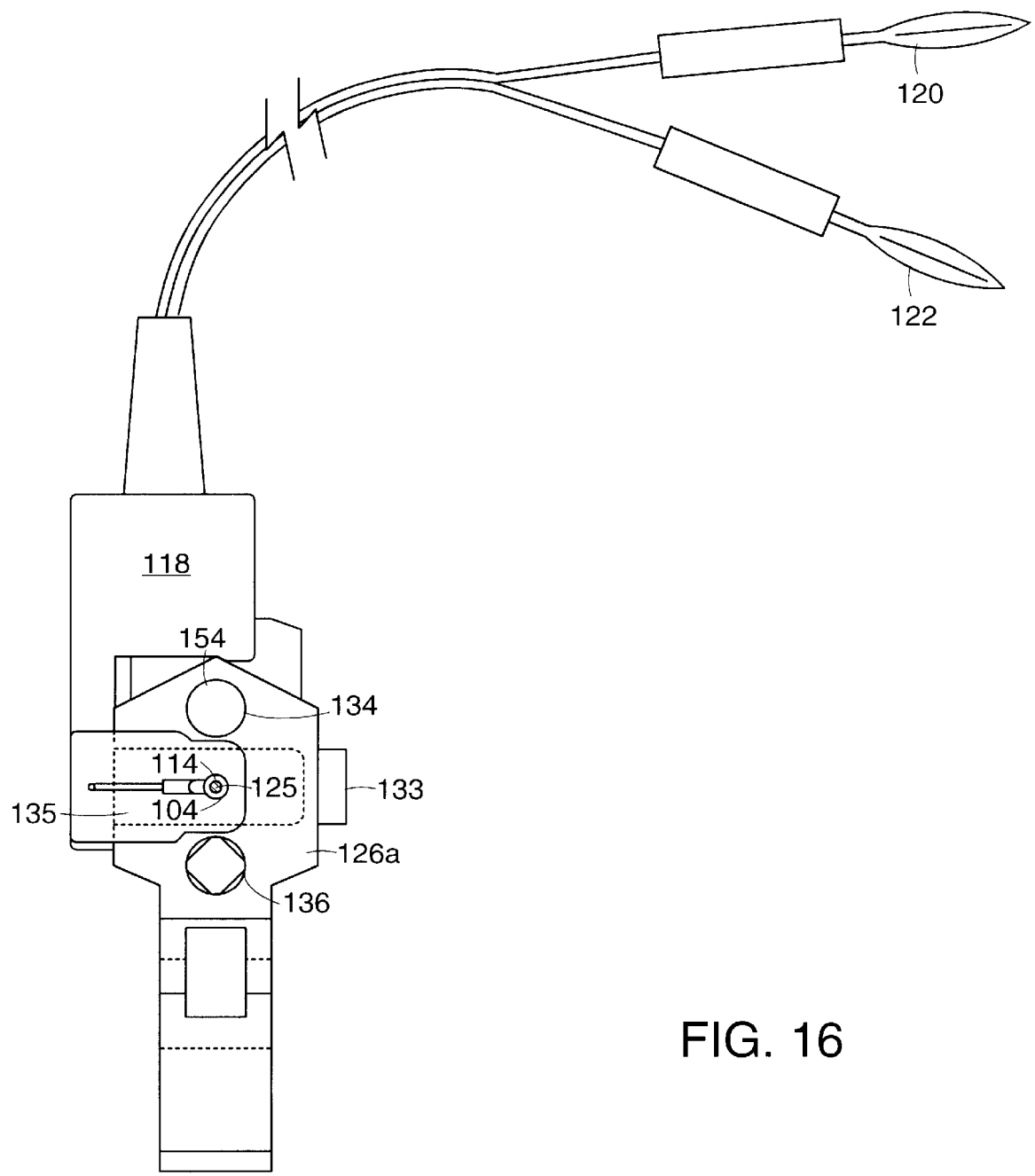
FIG. 16 is an enlarged partially cross-sectional view of a portion of the handle of the resectoscope of FIG. 12 and a bipolar power connector adaptor.

With reference to FIG. 16, power connector 118 is mounted on handle portion 126a of the resectoscope. Handle portion 126a includes an internal knife-edge lock (not shown in FIG. 16) that grasps bipolar electrosurgical device 104 once it has been inserted into aperture 125 of handle portion 126a. A push-button release mechanism 133 operates through an aperture 135 in handle portion 126a to release bipolar electrosurgical device 104 from the knife edge lock so that it can be removed from handle portion 126a.

Figure 17:
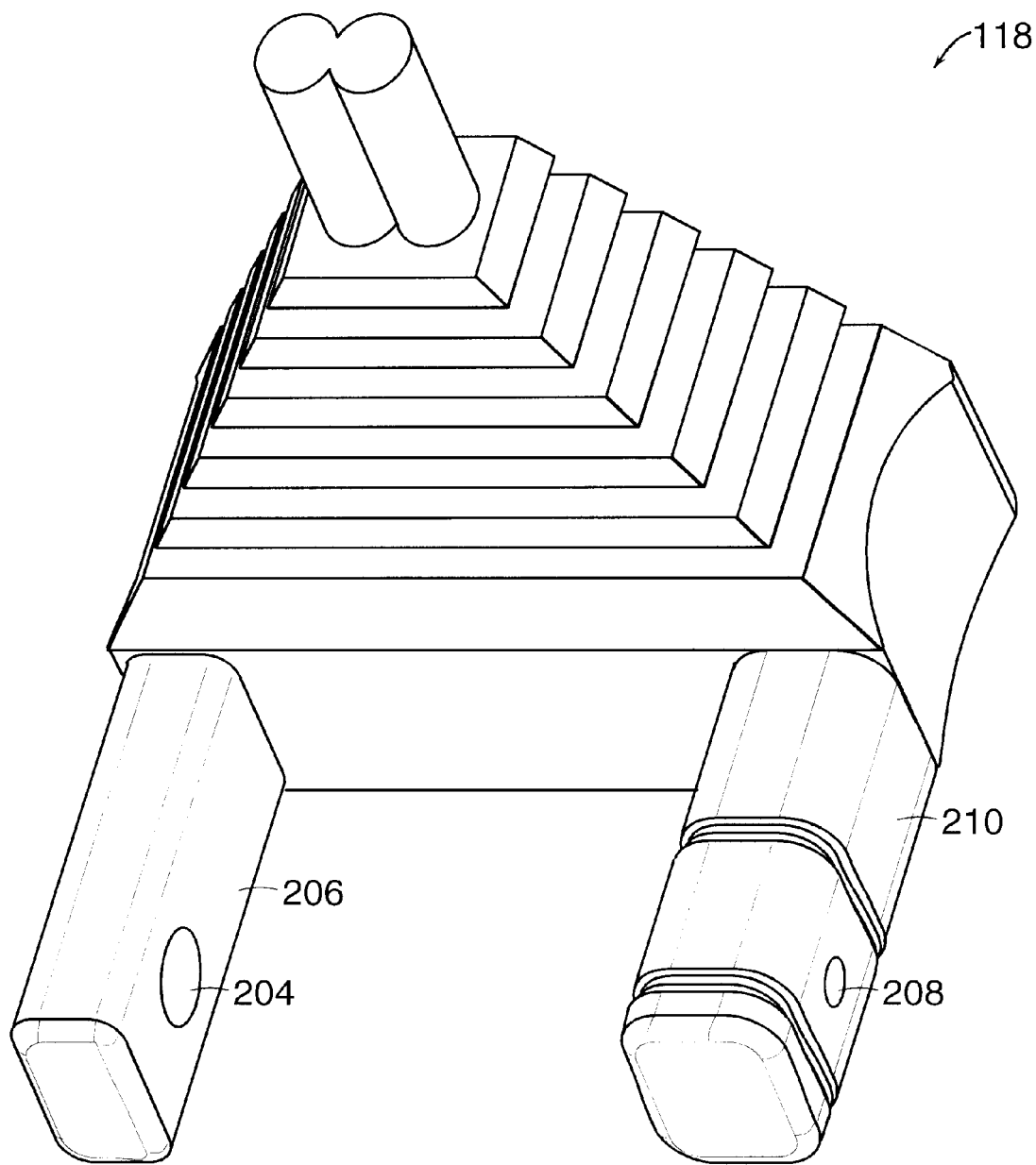
FIG. 17 is a perspective view of another bipolar power connector adaptor that can be used in conjunction with the resectoscope of FIG. 12.
Figure 18:
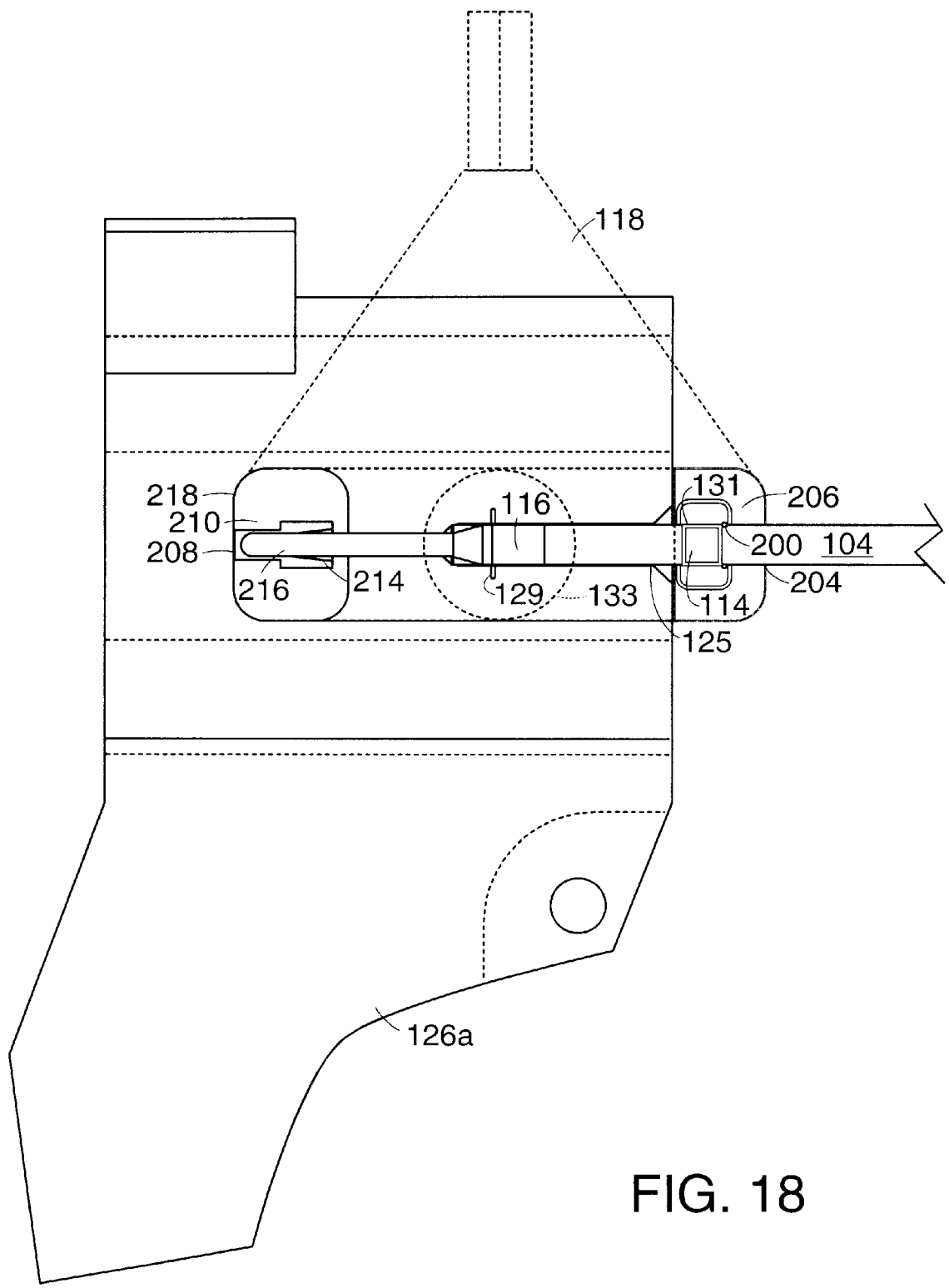
FIG. 18 is an enlarged side view of a portion of the handle of the resectoscope of FIG. 12 in combination with the bipolar power connector adaptor of FIG. 17.

FIGS. 17 and 18 illustrate one example of power connector 118 (note that the power connector shown in FIGS. 17 and 18 has a slightly different shape from the power connector shown in FIGS. 12, 13, 16, and 21a–21c). Power connector 118 (shown in dashed lines in FIG. 18) is an adaptor power connector that is attachable to an ACMI resectoscope, which is designed for use with a monopolar electro-surgical device, to allow a physician to perform bipolar electro-surgery. The adaptor power connector may be an insert molded part. Arm 210 of power connector adaptor 118 fits into a hole 218 in handle portion 126a of the resectoscope (hole 218 is designed to permit an electrical connection to be made to the proximal tip of a monopolar electro-surgical device). Arm 206 of power connector adaptor 118 fits immediately adjacent to the distal edge of handle portion 126a.

Pin 116 of bipolar electrosurgical device 104 is inserted through hole 204 in arm 206 of power connector adaptor 118, into an aperture 125 in handle portion 126a of resectoscope 102, and through hole 208 in arm 210 of power connector adaptor 118. Handle portion 126a of the resectoscope includes a knife edge lock 129 for grasping a slot in pin 116. As discussed above in connection with FIG. 16, push-button release mechanism 133 in handle portion 126a releases pin 116 from knife edge lock 129 so that bipolar electrosurgical device 104 can be removed from handle portion 126a. Arm 210 of power connector adaptor 118 includes a leaf spring connector 214 for grasping bullet tip 216 of pin 116 and electrically connecting to pin 116, and arm 206 of power connector adaptor 118 includes a leaf spring connector 131 for grasping ring 114 and electrically connecting to ring 114.

An O-ring or a silicone membrane (i.e., diaphragm or septum) 200 is placed at the opening 202 of hole 204 in power connector adaptor 118 to prevent liquid from entering the power connector adaptor and handle portion 126a and forming a conductive path between pin 116 and ring 114. Pin 116 is passed through the O-ring, diaphragm, or septum when the bipolar electro-surgical device is inserted within the power connector adaptor.

After a procedure is complete and the resectoscope is removed from the patient, bipolar electro-surgical device 104 is removed from the resectoscope using the push-button release and may be thrown away or cleaned. Prior to the next procedure, a physician may insert a new or cleaned electrosurgical device 104 within the resectoscope.

Figure 19:
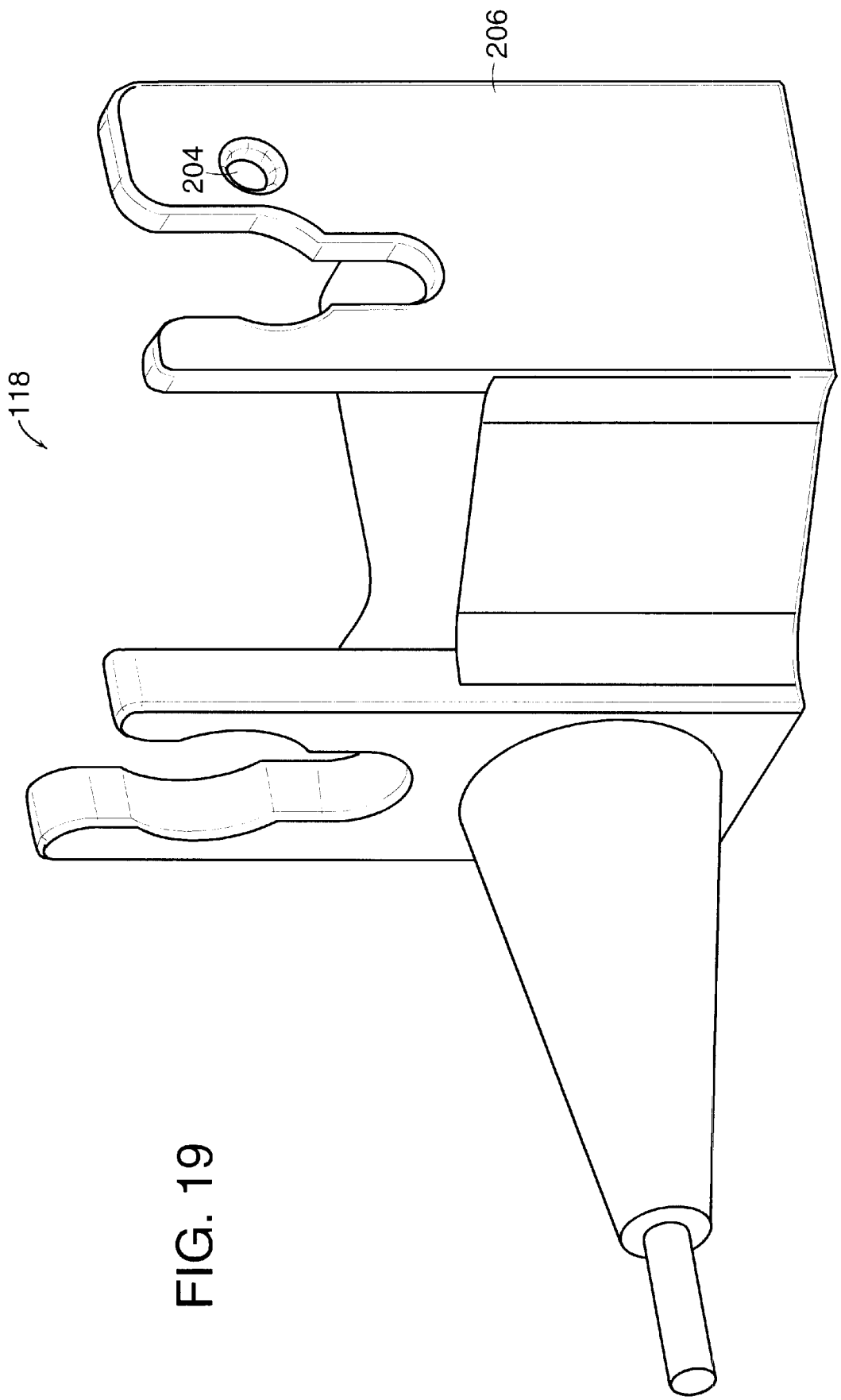
FIG. 19 is a perspective view of a power connector adaptor for use in conjunction with another type of resectoscope.
Figure 20:
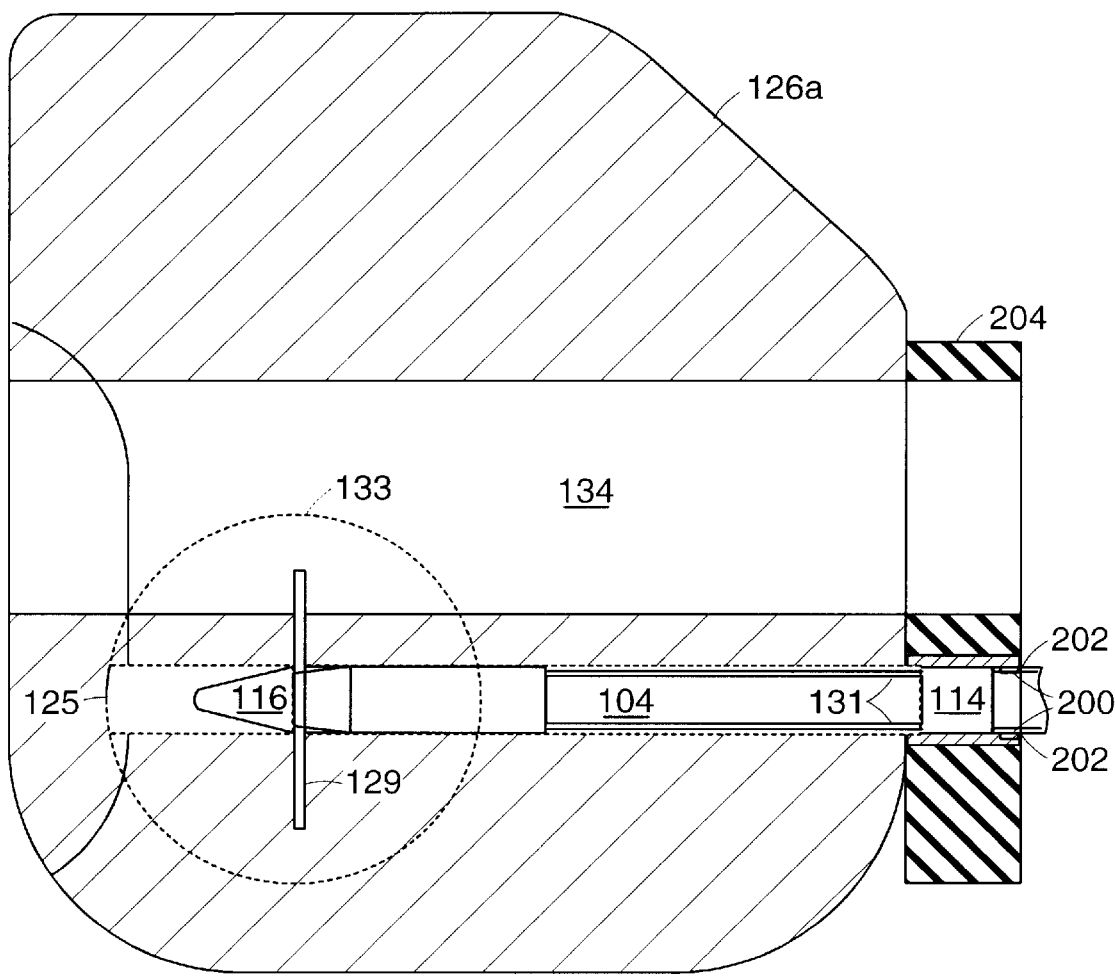
FIG. 20 is an enlarged side view, shown in partial cross-section, of the power connector adaptor of FIG. 18 and a portion of the handle of a resectoscope.

With reference to FIGS. 19 and 20, another power connector adaptor 118 is configured for use in conjunction with a Storz resectoscope rather than an ACMI resectoscope. Handle portion 126a of the Storz resectoscope includes a built-in mechanism (not shown) for electrically connecting to pin 116 of bipolar electro-surgical device 104, and power connector adaptor 118 includes a leaf spring connector 131 for grasping ring 114 and electrically connecting to ring 114. Pin 116 is inserted through 204 in arm 206 of power connector adaptor 118 and into an aperture 125 in handle portion 126a of resectoscope 102. Handle portion 126a of the resectoscope includes a push-button release mechanism 133 that operates through an aperture in handle portion 126a to release pin 116 from knife edge lock 129. An O-ring or a silicone membrane (i.e., diaphragm or septum) 200 is placed at the opening 202 of hole 204 in power connector adaptor 118 to prevent liquid from entering the power connector adaptor and handle portion 126a and forming a conductive path between pin 116 and ring 114.

Use

Figure 21C:
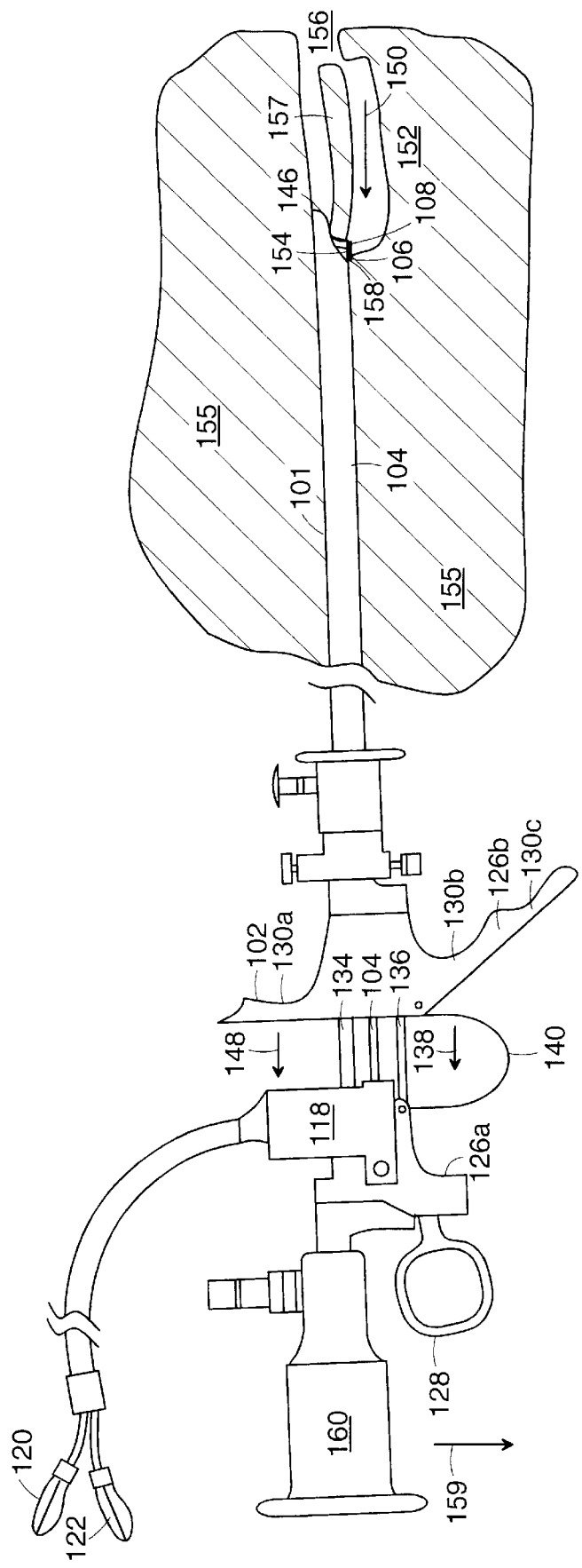

Referring to FIGS. 21a–21c, the operation of electrosurgical device 104 will be described with regard to a transurethral resectioning procedure (TURP). The patient is prepared by inserting a bullet-nosed obturator (not shown) within a sheath 101 (FIG. 13) to the region of treatment. The obturator is then removed from the sheath while leaving the sheath within the patient, and a resectoscope and bipolar electro-surgical device assembly is then inserted into the sheath. The assembly includes a telescope 160 that is inserted through rail 134 and a metal jacket 162 (FIG. 13) of resectoscope 102. With telescope 160 and irrigation, the physician inspects the region. The region is then flushed with saline.

Resectoscope 102 includes a two-piece handle having a proximal thumb piece 126a and a distal finger piece 126b. Power connector adaptor 118 is attached to thumb piece 126a. A physician inserts his thumb through ring 128 in thumb piece 126a and lays his fingers across indentations 130a, 130b, 130c in finger piece 126b and squeezes to slide (arrow 132, FIG. 21a) the thumb piece along rails 134, 136 against a force (arrow 138) provided by a spring 140. Sliding the thumb piece toward the finger piece pushes bipolar electro-surgical device 104 through metal jacket 124 in the resectoscope to cause electrodes 106, 108 to extend away from (arrow 142) distal end 123 (FIG. 13) of resectoscope 102 and a distal end 146 of sheath 101. Slide distance d6 (FIG. 21a) is equal to the distance d7 which the loop electrodes may be extended from the distal end of the sheath. The width W3 of the adaptor power connector is minimized to avoid decreasing the slide distance.

The physician applies power to the loop electrodes by turning on the RF generator and applies an upward pressure to the external end of resectoscope 102, as indicated by arrow 147, to bring the electrodes in contact with tissue 155. The physician then slowly releases his grip on the two-piece handle to allow the thumb piece to move away from (arrow 148, FIG. 21c) the finger piece and the electrodes to move back toward (arrow 150) the distal end of the sheath. As the electrodes are moved back toward the sheath, cutting electrode 106 resects a chip 152 of tissue from a resecting path 154 within the patient's urethra 156, and current 154 passing between the electrodes coagulates tissue in the area 157 of the incision. When the thumb piece of the handle is completely released, the electrodes are pulled back into the sheath and chip 152 is cut off against a lower portion 158 of the distal end of the sheath. The physician then either stops applying upward pressure to resectoscope 102 allowing urethra 156 to cause the resectoscope to move in a downward direction, indicated by arrow 159, or directly applies a downward force to move the resectoscope in the downward direction.

Other Embodiments

Many additional embodiments are possible. For example, the length L2 of coagulating electrode 14 (FIG. 2) can be cut with grooves (not shown) to increase the traction coagulating electrode 14 has with the tissue surface. Similarly, the surface of coagulating electrode 14 can be polished to prevent debris from sticking to coagulating electrode 14. Instead of using a roller electrode for coagulation, a sled electrode (i.e., does not roll, not shown) with the same surface area could be used. Coagulating electrode 14 is preferred, however, because as coagulating electrode 14 rolls (i.e., turns in direction 50) it prevents the build up of debris along resecting path 24. In yet another embodiment, instead of using a roller electrode for coagulation, a resilient coil wire with substantial "give" and with the same surface area could be used.

In other embodiments, a fluid flow directly over the electrodes may be provided to wash away char that could interfere with current flow. The flow could be provided by, for example, a small tube running through metal jacket 20 that terminates in a nozzle-form directed onto the electrode surfaces. In another example, the electrode and electrode lead could be hollow allowing fluid to flow and the working surface perforated such that fluid weeps from the electrode to wash away char. The fluid may be saline or another conductive fluid that does not inhibit current flow. Washing fluid flow can be initiated and terminated by a foot pedal, which may be the same foot pedal that turns on power.

Figure 10:
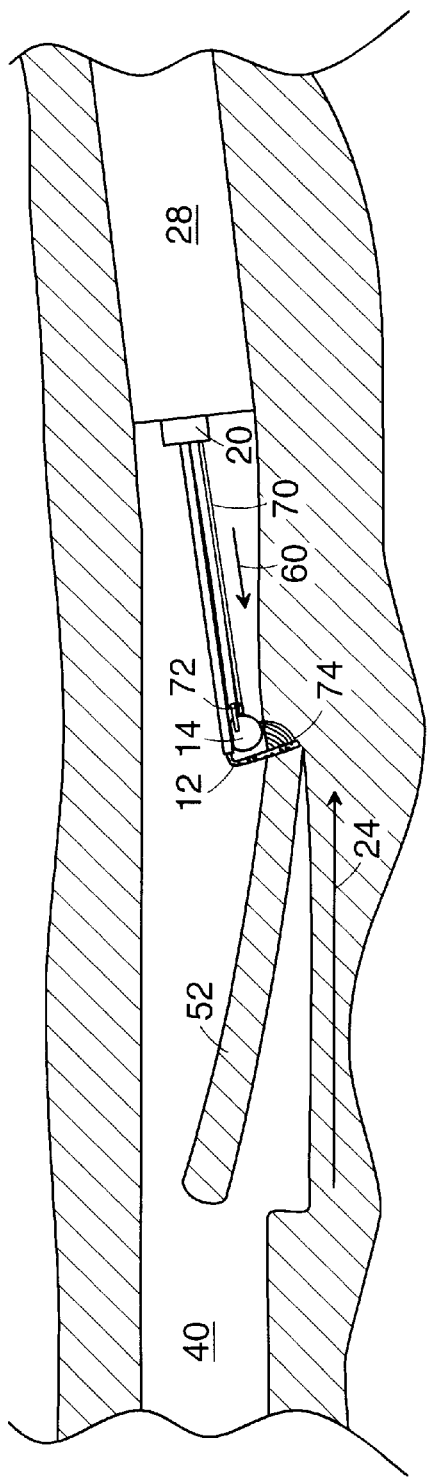
FIGS. 10 and 11 are cross-sectional side-views illustrating structure and use of another embodiment of an electro-surgical device.
Figure 11:
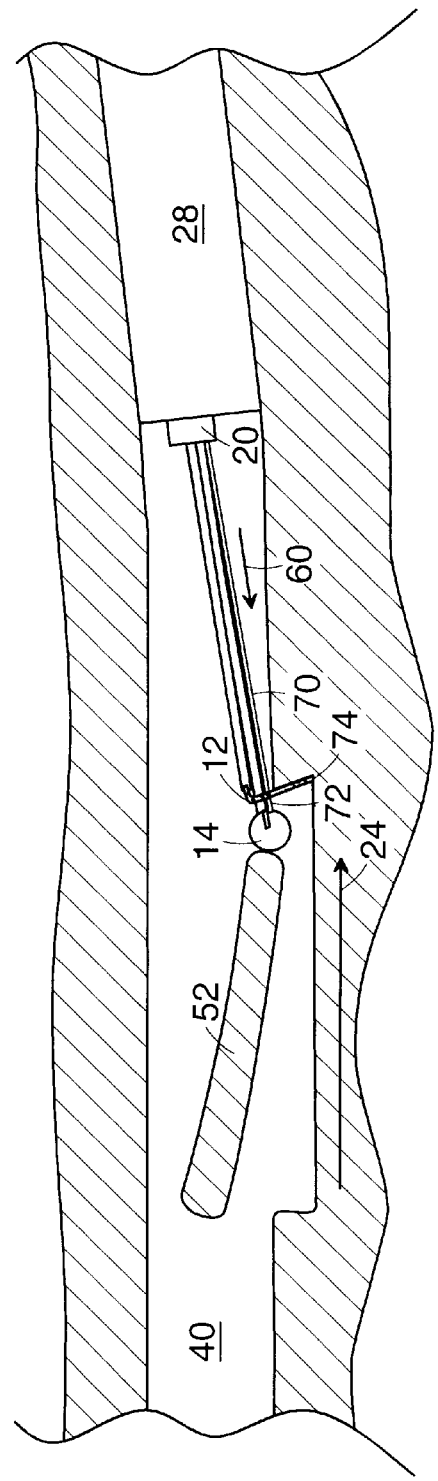

Referring to FIGS. 10 and 11, to avoid leaving excess coagulated tissue region 58 in place at the end of a cut, electrodes 12 and 14 can be configured to move in an axial direction (i.e., along resection path 24) independent of each other. This axial action can be achieved by passing the insulated leads to the resecting and coagulation electrodes through seperate lumens within sheath 20. When the physician reaches the end of resection path 24, the physician uses a mechanism to independently push coagulating electrode 14 back along resecting path 24 in an axial direction, indicated by arrow 60, until coagulating electrode 14 is on an opposite side of resecting electrode 12. As a result, coagulated tissue region 58 is removed as part of chip 52.

In order to move coagulating electrode 14 to an opposite side of resecting electrode 12, the width W2 (FIG. 2) of coagulating electrode 14 fork 46 is much smaller than the width W1 of resecting electrode 12 fork 48. Additionally, to prevent the two electrodes from coming in contact with each other, the length L2 of coagulating electrode 14 is made less than the length L1 of resecting electrode 12.

Allowing electrodes 12 and 14 to move in an axial direction independent of each other can also be used to change the direction of resection. Urging coagulating electrode 14 to an opposite side of resecting electrode 12 allows for coagulation and resection along a resecting path in a direction opposite to resecting path 24. Because a physician will normally carve several chips out of the urethra in a transurethral procedure, by changing the direction of the resecting path, the physician carves a chip out with each push and then with each pull of the device.

The electrodes may also include a flushing apparatus to remove char. A tube 70, extending from outside the device, terminates in a nozzle 72 that directs a flow of saline onto the roller. The resecting electrode is a hollow-form with perforations 74 through which saline can weep onto the working surface.

Coupling and pivoting mechanisms, other than the fork 46, 48 arrangement, can be employed. The maximum depth of resection may not be limited by a stop engagement. The resecting electrode can be constructed such that the coagulation electrode can pass beyond the mounting for the resecting electrode. If the width of the fork of the coagulating electrode is less than the width between the two loop halves of the resecting electrode, the depth of resection is not limited. Using the telescope 30, the physician can manually control the maximum depth of resection. Coagulation may be carried out just after resection, by reversing the orientation of the electrodes.

The electro-surgical devices can be constructed for use in various procedures, including endoscopic, laparoscopic (i.e., the electrode configuration extends through a trocar), and cystoscopic procedures. The device can have a flexible shaft for delivery deep into the body. The devices can be configured for removal or debulking of tumors in, e.g., the esophagus, cervix, or uterus (myomectomy), or for removal of liver lobe sections or removal of any protruding vascular tissue. The devices may also be configured to resect the lining of the uterus (endometrioma) or for use in transurethral resectioning of the bladder (TURB).

The devices can be constructed to carry multiple different resecting and/or coagulating electrodes among which power can be switched to vary the depth or width of treatment. For example, the device may carry two resecting loops arranged and of different size to allow cutting to different maximum depths. Differently shaped coagulating electrodes can be carried to vary the coagulation pattern. By switching among the different electrodes, the physician can tailor the treatment without removing the device from the body. The different electrodes can be arranged in parallel about or in series along the device axis. The power applied to the device can be varied with device construction and purpose (tissue type). Small scale devices, e.g., for use in the brain, may use lower power settings, e.g., 10 Watts. The arrangement can be adapted for a handheld device for use in open surgery. Moreover, the resecting electrode can be replaced with a different shaped small surface area resecting electrode, and the coagulating electrode can be replaced with a different shaped larger surface area coagulating electrode.

With reference to FIG. 22, there is shown a modified version of bipolar electro-surgical device 104 shown in FIG. 13. In the modified bipolar electro-surgical device, instead of providing a coagulation electrode (electrode 108 in FIG. 13), insulator jacket 112 is constructed to allow a steady stream of saline solution to be injected into the area to be coagulated. Insulator jacket 112 is constructed so as to maintain the saline solution in electrical contact with ring 114 or pin 116 at the proximal end of the bipolar electro-surgical device. The steady stream of saline solution functions as the equivalent of a thin, small-diameter wire and coagulates tissue in a manner similar to, and with the same effect as, the embodiment of FIG. 13. However, the embodiment of FIG. 22 has the advantage that the initial impedance across the output leads of the RF generator can be higher than the initial impedance in the embodiment of FIG. 13. This is important because certain RF generators are constructed, for safety reasons, to assume that if the initial impedance across the output leads is relatively low, a short circuit might be present. Under such conditions, the output current starts out low and then builds up as the RF generator learns that there is in fact no short circuit. The embodiment of FIG. 22, in contrast, can avoid this current build-up time.

With reference to FIGS. 23–25, there is shown another bipolar electrosurgical device, having wedge-like resection electrode 222 and loop return electrode 224 positioned at the ends of insulated wires 228 and 230. The bipolar electrosurgical device is positioned within an electrically conductive environment such as a saline field 232 that is injected through resectoscope sheath 226. When the bipolar electrosurgical device is extended as shown in FIG. 24 and resection electrode 222 is placed in contact with tissue, current passes from the resection electrode through the tissue and through saline 232 to return electrode 224, if the resectoscope sheath 226 is non-conductive. If the resectoscope sheath is conductive, current passes from resection electrode 222 through the tissue to resectoscope sheath 226, and then from the resectoscope sheath through saline 232 to return electrode 224. An alternative embodiment is shown in FIG. 26, in which resection electrode 222 is a wedge-like electrode as in FIGS. 23–25 but return electrode 224 is an exposed wire rather than a loop.

There have been described novel and improved apparatus and techniques for electro-surgical tissue removal. It is evident that those skilled in the art may now make numerous uses and modifications of and departures from the specific embodiment described herein without departing from the inventive concept. Consequently, other embodiments are within the following claims.

What is claimed is:

1. A bipolar electrosurgical apparatus electrically connectable to a power source, comprising:

a coagulation electrode having a relatively large surface area, the coagulation electrode comprising a roller electrode; and a resection electrode, mechanically coupled to the coagulation electrode and having a relatively small surface area, wherein when power from the power source is applied to the coagulation and resection electrodes, the coagulation electrode generates a diffuse current zone sufficient to heat a region of tissue to coagulation temperatures and the resection electrode generates a concentrated current region sufficient to heat tissue adjacent the resection electrode to resection temperatures;

the electrodes being relatively positioned along a treatment path such that tissue is coagulated and resected as the electro-surgical apparatus is disposed along the path.

2. A bipolar electrosurgical apparatus electrically connectable to a power source, comprising:

a coagulation electrode having a relatively large surface area, the coagulation electrode comprising a roller electrode; and a resection electrode, mechanically coupled to the coagulation electrode and having a relatively small surface area, the resection electrode comprising a loop electrode, wherein the coagulation electrode is positioned proximal to the resection electrode along a treatment path, such that tissue is coagulated prior to being resected to a desired depth as the bipolar electrosurgical device is moved along the treatment path, and wherein when power from the power source is applied to the coagulation and resection electrodes, the coagulation electrode generates a diffuse current zone sufficient to heat a region of tissue to coagulation temperatures and the resection electrode generates a concentrated current region sufficient to heat tissue adjacent the resection electrode to resection temperatures.

3. The apparatus of claim 2 wherein the mechanical coupling of the resection electrode to the coagulation electrode permits pivoting to vary the depth of treatment.

4. A method of bipolar electrosurgical tissue removal, comprising:

positioning a pair of bipolar electrodes along a first treatment path;

imposing a voltage differential to cause current to flow through tissue between the electrodes;

diffusing the current at a coagulation electrode to heat the tissue sufficiently to cause coagulation, the coagulation electrode comprising a roller electrode;

concentrating the current at a resection electrode sufficiently to cause resection of the tissue; and moving the coagulation and resection electrodes along the treatment path, such that the tissue is coagulated and resected.

* * * * *